US012788316B2

(12) United States Patent
Troxell et al.

(10) Patent No.: US 12,788,316 B2
(45) Date of Patent: Nov. 10, 2026

(54) IMPLANTABLE RF SENSOR FOR BIOFILM DETECTION

(71) Applicant: GLOBUS MEDICAL, INC., Audubon, PA (US)

(72) Inventors: Paden Troxell, Conshokocken, PA (US); David C. Paul, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 412 days.

(21) Appl. No.: 18/477,841

(22) Filed: Sep. 29, 2023

(65) Prior Publication Data

US 2025/0107751 A1 Apr. 3, 2025

(51) Int. Cl.
*A61B 5/00* (2006.01)

(52) U.S. Cl.
CPC .......... *A61B 5/4851* (2013.01); *A61B 5/0031* (2013.01); *A61B 5/686* (2013.01)

(58) Field of Classification Search
CPC ..... A61B 5/4851; A61B 5/0031; A61B 5/686; A61B 5/0507
See application file for complete search history.

(56) References Cited

U.S. PATENT DOCUMENTS 4,150,293 A 4/1979 Franke
5,246,010 A 9/1993 Gazzara et al.
5,354,314 A 10/1994 Hardy et al.
5,397,323 A 3/1995 Taylor et al.
5,598,453 A 1/1997 Baba et al.
5,772,594 A 6/1998 Barrick
5,791,908 A 8/1998 Gillio
5,820,559 A 10/1998 Ng et al.
5,825,982 A 10/1998 Wright et al.
5,887,121 A 3/1999 Funda et al.
5,911,449 A 6/1999 Daniele et al.
5,951,475 A 9/1999 Gueziec et al.
5,987,960 A 11/1999 Messner et al.
6,012,216 A 1/2000 Esteves et al.
6,031,888 A 2/2000 Ivan et al.
6,033,415 A 3/2000 Mittelstadt et al.
6,080,181 A 6/2000 Jensen et al.
6,106,511 A 8/2000 Jensen
6,122,541 A 9/2000 Cosman et al.
6,144,875 A 11/2000 Schweikard et al.
6,157,853 A 12/2000 Blume et al.
6,167,145 A 12/2000 Foley et al.

(Continued)

OTHER PUBLICATIONS

US 8,231,638 B2, 07/2012, Swarup et al. (withdrawn)

(Continued)

*Primary Examiner* — Joseph M Dietrich

(57) ABSTRACT

A medical implant includes an implant component configured to be implanted in a patient, a radio frequency (RF) transmit antenna in the implant component and configured to transmit a RF signal, and circuitry within the implant component. The circuitry is operative to generate the RF signal to the RF transmit antenna, determine a characteristic of attenuation of the RF signal when the RF transmit antenna is transmitting the RF signal while implanted in the patient, and detect presence of biofilm on the medical implant based on the characteristic of attenuation of the RF signal.

17 Claims, 10 Drawing Sheets

(56) References Cited

U.S. PATENT DOCUMENTS 6,167,292 A 12/2000 Badano et al.
6,201,984 B1 3/2001 Funda et al.
6,203,196 B1 3/2001 Meyer et al.
6,205,411 B1 3/2001 DiGioia et al.
6,212,419 B1 4/2001 Blume et al.
6,231,565 B1 5/2001 Tovey et al.
6,236,875 B1 5/2001 Bucholz et al.
6,246,900 B1 6/2001 Cosman et al.
6,301,495 B1 10/2001 Gueziec et al.
6,306,126 B1 10/2001 Montezuma
6,312,435 B1 11/2001 Wallace et al.
6,314,311 B1 11/2001 Williams et al.
6,320,929 B1 11/2001 Von Der Haar
6,322,567 B1 11/2001 Mittelstadt et al.
6,325,808 B1 12/2001 Bernard et al.
6,340,363 B1 1/2002 Bolger et al.
6,377,011 B1 4/2002 Ben-Ur
6,379,302 B1 4/2002 Kessman et al.
6,402,762 B2 6/2002 Hunter et al.
6,424,885 B1 7/2002 Niemeyer et al.
6,447,503 B1 9/2002 Wynne et al.
6,451,027 B1 9/2002 Cooper et al.
6,477,400 B1 11/2002 Barrick
6,484,049 B1 11/2002 Seeley et al.
6,487,267 B1 11/2002 Wolter
6,490,467 B1 12/2002 Bucholz et al.
6,490,475 B1 12/2002 Seeley et al.
6,499,488 B1 12/2002 Hunter et al.
6,501,981 B1 12/2002 Schweikard et al.
6,507,751 B2 1/2003 Blume et al.
6,535,756 B1 3/2003 Simon et al.
6,560,354 B1 5/2003 Maurer, Jr. et al.
6,565,554 B1 5/2003 Niemeyer
6,587,750 B2 7/2003 Gerbi et al.
6,614,453 B1 9/2003 Suri et al.
6,614,871 B1 9/2003 Kobiki et al.
6,619,840 B2 9/2003 Rasche et al.
6,636,757 B1 10/2003 Jascob et al.
6,645,196 B1 11/2003 Nixon et al.
6,666,579 B2 12/2003 Jensen
6,669,635 B2 12/2003 Kessman et al.
6,701,173 B2 3/2004 Nowinski et al.
6,757,068 B2 6/2004 Foxlin
6,782,287 B2 8/2004 Grzeszczuk et al.
6,783,524 B2 8/2004 Anderson et al.
6,786,896 B1 9/2004 Madhani et al.
6,788,018 B1 9/2004 Blumenkranz
6,804,581 B2 10/2004 Wang et al.
6,823,207 B1 11/2004 Jensen et al.
6,827,351 B2 12/2004 Graziani et al.
6,837,892 B2 1/2005 Shoham
6,839,612 B2 1/2005 Sanchez et al.
6,856,826 B2 2/2005 Seeley et al.
6,856,827 B2 2/2005 Seeley et al.
6,879,880 B2 4/2005 Nowlin et al.
6,892,090 B2 5/2005 Verard et al.
6,920,347 B2 7/2005 Simon et al.
6,922,632 B2 7/2005 Foxlin
6,968,224 B2 11/2005 Kessman et al.
6,978,166 B2 12/2005 Foley et al.
6,988,009 B2 1/2006 Grimm et al.
6,991,627 B2 1/2006 Madhani et al.
6,996,487 B2 2/2006 Jutras et al.
6,999,852 B2 2/2006 Green
7,007,699 B2 3/2006 Martinelli et al.
7,016,457 B1 3/2006 Senzig et al.
7,043,961 B2 5/2006 Pandey et al.
7,062,006 B1 6/2006 Pelc et al.
7,063,705 B2 6/2006 Young et al.
7,072,707 B2 7/2006 Galloway, Jr. et al.
7,083,615 B2 8/2006 Peterson et al.
7,097,640 B2 8/2006 Wang et al.
7,099,428 B2 8/2006 Clinthorne et al.
7,108,421 B2 9/2006 Gregerson et al.
7,130,676 B2 10/2006 Barrick
7,139,418 B2 11/2006 Abovitz et al.
7,139,601 B2 11/2006 Bucholz et al.
7,155,316 B2 12/2006 Sutherland et al.
7,164,968 B2 1/2007 Treat et al.
7,167,738 B2 1/2007 Schweikard et al.
7,169,141 B2 1/2007 Brock et al.
7,172,627 B2 2/2007 Fiere et al.
7,194,120 B2 3/2007 Wicker et al.
7,197,107 B2 3/2007 Arai et al.
7,231,014 B2 6/2007 Levy
7,231,063 B2 6/2007 Naimark et al.
7,239,940 B2 7/2007 Wang et al.
7,248,914 B2 7/2007 Hastings et al.
7,301,648 B2 11/2007 Foxlin
7,302,288 B1 11/2007 Schellenberg
7,313,430 B2 12/2007 Urquhart et al.
7,318,805 B2 1/2008 Schweikard et al.
7,318,827 B2 1/2008 Leitner et al.
7,319,897 B2 1/2008 Leitner et al.
7,324,623 B2 1/2008 Heuscher et al.
7,327,865 B2 2/2008 Fu et al.
7,331,967 B2 2/2008 Lee et al.
7,333,642 B2 2/2008 Green
7,339,341 B2 3/2008 Oleynikov et al.
7,366,562 B2 4/2008 Dukesherer et al.
7,379,790 B2 5/2008 Toth et al.
7,386,365 B2 6/2008 Nixon
7,422,592 B2 9/2008 Morley et al.
7,435,216 B2 10/2008 Kwon et al.
7,440,793 B2 10/2008 Chauhan et al.
7,460,637 B2 12/2008 Clinthorne et al.
7,466,303 B2 12/2008 Yi et al.
7,493,153 B2 2/2009 Ahmed et al.
7,505,617 B2 3/2009 Fu et al.
7,533,892 B2 5/2009 Schena et al.
7,542,791 B2 6/2009 Mire et al.
7,555,331 B2 6/2009 Viswanathan
7,567,834 B2 7/2009 Clayton et al.
7,594,912 B2 9/2009 Cooper et al.
7,606,613 B2 10/2009 Simon et al.
7,607,440 B2 10/2009 Coste-Maniere et al.
7,623,902 B2 11/2009 Pacheco
7,630,752 B2 12/2009 Viswanathan
7,630,753 B2 12/2009 Simon et al.
7,643,862 B2 1/2010 Schoenefeld
7,660,623 B2 2/2010 Hunter et al.
7,661,881 B2 2/2010 Gregerson et al.
7,683,331 B2 3/2010 Chang
7,683,332 B2 3/2010 Chang
7,689,320 B2 3/2010 Prisco et al.
7,691,098 B2 4/2010 Wallace et al.
7,702,379 B2 4/2010 Avinash et al.
7,702,477 B2 4/2010 Tuemmler et al.
7,711,083 B2 5/2010 Heigl et al.
7,711,406 B2 5/2010 Kuhn et al.
7,720,523 B2 5/2010 Omernick et al.
7,725,253 B2 5/2010 Foxlin
7,726,171 B2 6/2010 Langlotz et al.
7,742,801 B2 6/2010 Neubauer et al.
7,751,865 B2 7/2010 Jascob et al.
7,760,849 B2 7/2010 Zhang
7,762,825 B2 7/2010 Burbank et al.
7,763,015 B2 7/2010 Cooper et al.
7,787,699 B2 8/2010 Mahesh et al.
7,796,728 B2 9/2010 Bergfjord
7,813,838 B2 10/2010 Sommer
7,818,044 B2 10/2010 Dukesherer et al.
7,819,859 B2 10/2010 Prisco et al.
7,824,401 B2 11/2010 Manzo et al.
7,831,294 B2 11/2010 Viswanathan
7,834,484 B2 11/2010 Sartor
7,835,557 B2 11/2010 Kendrick et al.
7,835,778 B2 11/2010 Foley et al.
7,835,784 B2 11/2010 Mire et al.
7,840,253 B2 11/2010 Tremblay et al.
7,840,256 B2 11/2010 Lakin et al.
7,843,158 B2 11/2010 Prisco
7,844,320 B2 11/2010 Shahidi
7,853,305 B2 12/2010 Simon et al.

(56) References Cited

U.S. PATENT DOCUMENTS

| | | | |
|---|---|---|---|
| 7,853,313 | B2 | 12/2010 | Thompson |
| 7,865,269 | B2 | 1/2011 | Prisco et al. |
| D631,966 | S | 2/2011 | Perloff et al. |
| 7,879,045 | B2 | 2/2011 | Gielen et al. |
| 7,881,767 | B2 | 2/2011 | Strommer et al. |
| 7,881,770 | B2 | 2/2011 | Melkent et al. |
| 7,886,743 | B2 | 2/2011 | Cooper et al. |
| RE42,194 | E | 3/2011 | Foley et al. |
| RE42,226 | E | 3/2011 | Foley et al. |
| 7,900,524 | B2 | 3/2011 | Calloway et al. |
| 7,907,166 | B2 | 3/2011 | Lamprecht et al. |
| 7,909,122 | B2 | 3/2011 | Schena et al. |
| 7,925,653 | B2 | 4/2011 | Saptharishi |
| 7,930,065 | B2 | 4/2011 | Larkin et al. |
| 7,935,130 | B2 | 5/2011 | Willliams |
| 7,940,999 | B2 | 5/2011 | Liao et al. |
| 7,945,012 | B2 | 5/2011 | Ye et al. |
| 7,945,021 | B2 | 5/2011 | Shapiro et al. |
| 7,953,470 | B2 | 5/2011 | Vetter et al. |
| 7,954,397 | B2 | 6/2011 | Choi et al. |
| 7,971,341 | B2 | 7/2011 | Dukesherer et al. |
| 7,974,674 | B2 | 7/2011 | Hauck et al. |
| 7,974,677 | B2 | 7/2011 | Mire et al. |
| 7,974,681 | B2 | 7/2011 | Wallace et al. |
| 7,979,157 | B2 | 7/2011 | Anvari |
| 7,983,733 | B2 | 7/2011 | Viswanathan |
| 7,988,215 | B2 | 8/2011 | Seibold |
| 7,996,110 | B2 | 8/2011 | Lipow et al. |
| 8,004,121 | B2 | 8/2011 | Sartor |
| 8,004,229 | B2 | 8/2011 | Nowlin et al. |
| 8,010,177 | B2 | 8/2011 | Csavoy et al. |
| 8,019,045 | B2 | 9/2011 | Kato |
| 8,021,310 | B2 | 9/2011 | Sanborn et al. |
| 8,035,685 | B2 | 10/2011 | Jensen |
| 8,046,054 | B2 | 10/2011 | Kim et al. |
| 8,046,057 | B2 | 10/2011 | Clarke |
| 8,052,688 | B2 | 11/2011 | Wolf, II |
| 8,054,184 | B2 | 11/2011 | Cline et al. |
| 8,054,752 | B2 | 11/2011 | Druke et al. |
| 8,057,397 | B2 | 11/2011 | Li et al. |
| 8,057,407 | B2 | 11/2011 | Martinelli et al. |
| 8,062,288 | B2 | 11/2011 | Cooper et al. |
| 8,062,375 | B2 | 11/2011 | Glerum et al. |
| 8,066,524 | B2 | 11/2011 | Burbank et al. |
| 8,073,335 | B2 | 12/2011 | Labonville et al. |
| 8,079,950 | B2 | 12/2011 | Stern et al. |
| 8,086,299 | B2 | 12/2011 | Adler et al. |
| 8,092,370 | B2 | 1/2012 | Roberts et al. |
| 8,098,914 | B2 | 1/2012 | Liao et al. |
| 8,100,950 | B2 | 1/2012 | St. Clair et al. |
| 8,105,320 | B2 | 1/2012 | Manzo |
| 8,108,025 | B2 | 1/2012 | Csavoy et al. |
| 8,109,877 | B2 | 2/2012 | Moctezuma de Ll Barrera et al. |
| 8,112,292 | B2 | 2/2012 | Simon |
| 8,116,430 | B1 | 2/2012 | Shapiro et al. |
| 8,120,301 | B2 | 2/2012 | Goldberg et al. |
| 8,121,249 | B2 | 2/2012 | Wang et al. |
| 8,123,675 | B2 | 2/2012 | Funda et al. |
| 8,133,229 | B1 | 3/2012 | Bonutti |
| 8,142,420 | B2 | 3/2012 | Schena |
| 8,147,494 | B2 | 4/2012 | Leitner et al. |
| 8,150,494 | B2 | 4/2012 | Simon et al. |
| 8,150,497 | B2 | 4/2012 | Gielen et al. |
| 8,150,498 | B2 | 4/2012 | Gielen et al. |
| 8,165,658 | B2 | 4/2012 | Waynik et al. |
| 8,170,313 | B2 | 5/2012 | Kendrick et al. |
| 8,179,073 | B2 | 5/2012 | Farritor et al. |
| 8,182,476 | B2 | 5/2012 | Julian et al. |
| 8,184,880 | B2 | 5/2012 | Zhao et al. |
| 8,202,278 | B2 | 6/2012 | Orban, III et al. |
| 8,208,708 | B2 | 6/2012 | Homan et al. |
| 8,208,988 | B2 | 6/2012 | Jensen |
| 8,219,177 | B2 | 7/2012 | Smith et al. |
| 8,219,178 | B2 | 7/2012 | Smith et al. |
| 8,220,468 | B2 | 7/2012 | Cooper et al. |
| 8,224,024 | B2 | 7/2012 | Foxlin et al. |
| 8,224,484 | B2 | 7/2012 | Swarup et al. |
| 8,225,798 | B2 | 7/2012 | Baldwin et al. |
| 8,228,368 | B2 | 7/2012 | Zhao et al. |
| 8,231,610 | B2 | 7/2012 | Jo et al. |
| 8,239,001 | B2 | 8/2012 | Verard et al. |
| 8,241,271 | B2 | 8/2012 | Millman et al. |
| 8,248,413 | B2 | 8/2012 | Gattani et al. |
| 8,256,319 | B2 | 9/2012 | Cooper et al. |
| 8,263,933 | B2 | 9/2012 | Zeile |
| 8,271,069 | B2 | 9/2012 | Jascob et al. |
| 8,271,130 | B2 | 9/2012 | Hourtash |
| 8,281,670 | B2 | 10/2012 | Larkin et al. |
| 8,282,653 | B2 | 10/2012 | Nelson et al. |
| 8,301,226 | B2 | 10/2012 | Csavoy et al. |
| 8,311,611 | B2 | 11/2012 | Csavoy et al. |
| 8,320,991 | B2 | 11/2012 | Jascob et al. |
| 8,332,012 | B2 | 12/2012 | Kienzle, III |
| 8,333,755 | B2 | 12/2012 | Cooper et al. |
| 8,335,552 | B2 | 12/2012 | Stiles |
| 8,335,557 | B2 | 12/2012 | Maschke |
| 8,348,931 | B2 | 1/2013 | Cooper et al. |
| 8,353,963 | B2 | 1/2013 | Glerum |
| 8,358,818 | B2 | 1/2013 | Miga et al. |
| 8,359,730 | B2 | 1/2013 | Burg et al. |
| 8,374,673 | B2 | 2/2013 | Adcox et al. |
| 8,374,723 | B2 | 2/2013 | Zhao et al. |
| 8,379,791 | B2 | 2/2013 | Forthmann et al. |
| 8,386,019 | B2 | 2/2013 | Camus et al. |
| 8,392,022 | B2 | 3/2013 | Ortmaier et al. |
| 8,394,099 | B2 | 3/2013 | Patwardhan |
| 8,395,342 | B2 | 3/2013 | Prisco |
| 8,398,634 | B2 | 3/2013 | Manzo et al. |
| 8,400,094 | B2 | 3/2013 | Schena |
| 8,414,957 | B2 | 4/2013 | Enzerink et al. |
| 8,418,073 | B2 | 4/2013 | Mohr et al. |
| 8,450,694 | B2 | 5/2013 | Baviera et al. |
| 8,452,447 | B2 | 5/2013 | Nixon |
| RE44,305 | E | 6/2013 | Foley et al. |
| 8,462,911 | B2 | 6/2013 | Vesel et al. |
| 8,465,476 | B2 | 6/2013 | Rogers et al. |
| 8,465,771 | B2 | 6/2013 | Wan et al. |
| 8,467,851 | B2 | 6/2013 | Mire et al. |
| 8,467,852 | B2 | 6/2013 | Csavoy et al. |
| 8,469,947 | B2 | 6/2013 | Devengenzo et al. |
| RE44,392 | E | 7/2013 | Hynes |
| 8,483,434 | B2 | 7/2013 | Buehner et al. |
| 8,483,800 | B2 | 7/2013 | Jensen et al. |
| 8,486,532 | B2 | 7/2013 | Enzerink et al. |
| 8,489,235 | B2 | 7/2013 | Moll et al. |
| 8,500,722 | B2 | 8/2013 | Cooper |
| 8,500,728 | B2 | 8/2013 | Newton et al. |
| 8,504,201 | B2 | 8/2013 | Moll et al. |
| 8,506,555 | B2 | 8/2013 | Ruiz Morales |
| 8,506,556 | B2 | 8/2013 | Schena |
| 8,508,173 | B2 | 8/2013 | Goldberg et al. |
| 8,512,318 | B2 | 8/2013 | Tovey et al. |
| 8,515,576 | B2 | 8/2013 | Lipow et al. |
| 8,518,120 | B2 | 8/2013 | Glerum et al. |
| 8,521,331 | B2 | 8/2013 | Itkowitz |
| 8,526,688 | B2 | 9/2013 | Groszmann et al. |
| 8,526,700 | B2 | 9/2013 | Isaacs |
| 8,527,094 | B2 | 9/2013 | Kumar et al. |
| 8,528,440 | B2 | 9/2013 | Morley et al. |
| 8,532,741 | B2 | 9/2013 | Heruth et al. |
| 8,541,970 | B2 | 9/2013 | Nowlin et al. |
| 8,548,563 | B2 | 10/2013 | Simon et al. |
| 8,549,732 | B2 | 10/2013 | Burg et al. |
| 8,551,114 | B2 | 10/2013 | Ramos de la Pena |
| 8,551,116 | B2 | 10/2013 | Julian et al. |
| 8,556,807 | B2 | 10/2013 | Scott et al. |
| 8,556,979 | B2 | 10/2013 | Glerum et al. |
| 8,560,118 | B2 | 10/2013 | Green et al. |
| 8,561,473 | B2 | 10/2013 | Blumenkranz |
| 8,562,594 | B2 | 10/2013 | Cooper et al. |
| 8,571,638 | B2 | 10/2013 | Shoham |
| 8,571,710 | B2 | 10/2013 | Coste-Maniere et al. |
| 8,573,465 | B2 | 11/2013 | Shelton, IV |
| 8,574,303 | B2 | 11/2013 | Sharkey et al. |

(56) References Cited

U.S. PATENT DOCUMENTS 8,585,420 B2 11/2013 Burbank et al.
8,594,841 B2 11/2013 Zhao et al.
8,597,198 B2 12/2013 Sanborn et al.
8,600,478 B2 12/2013 Verard et al.
8,603,077 B2 12/2013 Cooper et al.
8,611,985 B2 12/2013 Lavallee et al.
8,613,230 B2 12/2013 Blumenkranz et al.
8,621,939 B2 1/2014 Blumenkranz et al.
8,624,537 B2 1/2014 Nowlin et al.
8,630,389 B2 1/2014 Kato
8,634,897 B2 1/2014 Simon et al.
8,634,957 B2 1/2014 Toth et al.
8,638,056 B2 1/2014 Goldberg et al.
8,638,057 B2 1/2014 Goldberg et al.
8,639,000 B2 1/2014 Zhao et al.
8,641,726 B2 2/2014 Bonutti
8,644,907 B2 2/2014 Hartmann et al.
8,657,809 B2 2/2014 Schoepp
8,660,635 B2 2/2014 Simon et al.
8,666,544 B2 3/2014 Moll et al.
8,675,939 B2 3/2014 Moctezuma de la Barrera
8,678,647 B2 3/2014 Gregerson et al.
8,679,125 B2 3/2014 Smith et al.
8,679,183 B2 3/2014 Glerum et al.
8,682,413 B2 3/2014 Lloyd
8,684,253 B2 4/2014 Giordano et al.
8,685,098 B2 4/2014 Glerum et al.
8,693,730 B2 4/2014 Umasuthan et al.
8,694,075 B2 4/2014 Groszmann et al.
8,696,458 B2 4/2014 Foxlin et al.
8,700,123 B2 4/2014 Okamura et al.
8,706,086 B2 4/2014 Glerum
8,706,185 B2 4/2014 Foley et al.
8,706,301 B2 4/2014 Zhao et al.
8,717,430 B2 5/2014 Simon et al.
8,727,618 B2 5/2014 Maschke et al.
8,734,432 B2 5/2014 Tuma et al.
8,738,115 B2 5/2014 Amberg et al.
8,738,181 B2 5/2014 Greer et al.
8,740,882 B2 6/2014 Jun et al.
8,746,252 B2 6/2014 McGrogan et al.
8,749,189 B2 6/2014 Nowlin et al.
8,749,190 B2 6/2014 Nowlin et al.
8,761,930 B2 6/2014 Nixon
8,764,448 B2 7/2014 Yang et al.
8,771,170 B2 7/2014 Mesallum et al.
8,781,186 B2 7/2014 Clements et al.
8,781,630 B2 7/2014 Banks et al.
8,784,385 B2 7/2014 Boyden et al.
8,786,241 B2 7/2014 Nowlin et al.
8,787,520 B2 7/2014 Baba
8,792,704 B2 7/2014 Isaacs
8,798,231 B2 8/2014 Notohara et al.
8,800,838 B2 8/2014 Shelton, IV
8,808,164 B2 8/2014 Hoffman et al.
8,812,077 B2 8/2014 Dempsey
8,814,793 B2 8/2014 Brabrand
8,816,628 B2 8/2014 Nowlin et al.
8,818,105 B2 8/2014 Myronenko et al.
8,820,605 B2 9/2014 Shelton, IV
8,821,511 B2 9/2014 Von Jako et al.
8,823,308 B2 9/2014 Nowlin et al.
8,827,996 B2 9/2014 Scott et al.
8,828,024 B2 9/2014 Farritor et al.
8,830,224 B2 9/2014 Zhao et al.
8,834,489 B2 9/2014 Cooper et al.
8,834,490 B2 9/2014 Bonutti
8,838,270 B2 9/2014 Druke et al.
8,844,789 B2 9/2014 Shelton, IV et al.
8,855,822 B2 10/2014 Bartol et al.
8,858,598 B2 10/2014 Seifert et al.
8,860,753 B2 10/2014 Bhandarkar et al.
8,864,751 B2 10/2014 Prisco et al.
8,864,798 B2 10/2014 Weiman et al.
8,864,833 B2 10/2014 Glerum et al.
8,867,703 B2 10/2014 Shapiro et al.
8,870,880 B2 10/2014 Himmelberger et al.
8,876,866 B2 11/2014 Zappacosta et al.
8,880,223 B2 11/2014 Raj et al.
8,882,803 B2 11/2014 Iott et al.
8,883,210 B1 11/2014 Truncale et al.
8,888,821 B2 11/2014 Rezach et al.
8,888,853 B2 11/2014 Glerum et al.
8,888,854 B2 11/2014 Glerum et al.
8,894,652 B2 11/2014 Seifert et al.
8,894,688 B2 11/2014 Suh
8,894,691 B2 11/2014 Iott et al.
8,906,069 B2 12/2014 Hansell et al.
8,964,934 B2 2/2015 Ein-Gal
8,992,580 B2 3/2015 Bar et al.
8,996,169 B2 3/2015 Lightcap et al.
9,001,963 B2 4/2015 Sowards-Emmerd et al.
9,002,076 B2 4/2015 Khadem et al.
9,044,190 B2 6/2015 Rubner et al.
9,107,683 B2 8/2015 Hourtash et al.
9,125,556 B2 9/2015 Zehavi et al.
9,131,986 B2 9/2015 Greer et al.
9,215,968 B2 12/2015 Schostek et al.
9,308,050 B2 4/2016 Kostrzewski et al.
9,380,984 B2 7/2016 Li et al.
9,393,039 B2 7/2016 Lechner et al.
9,398,886 B2 7/2016 Gregerson et al.
9,398,890 B2 7/2016 Dong et al.
9,414,859 B2 8/2016 Ballard et al.
9,420,975 B2 8/2016 Gutfleisch et al.
9,492,235 B2 11/2016 Hourtash et al.
9,592,096 B2 3/2017 Maillet et al.
9,750,465 B2 9/2017 Engel et al.
9,757,203 B2 9/2017 Hourtash et al.
9,795,354 B2 10/2017 Menegaz et al.
9,814,535 B2 11/2017 Bar et al.
9,820,783 B2 11/2017 Donner et al.
9,833,265 B2 12/2017 Donner et al.
9,848,922 B2 12/2017 Tohmeh et al.
9,925,011 B2 3/2018 Gombert et al.
9,931,025 B1 4/2018 Graetzel et al.
10,034,717 B2 7/2018 Miller et al.
2001/0036302 A1 11/2001 Miller
2002/0035321 A1 3/2002 Bucholz et al.
2004/0068172 A1 4/2004 Nowinski et al.
2004/0076259 A1 4/2004 Jensen et al.
2005/0096502 A1 5/2005 Khalili
2005/0143651 A1 6/2005 Verard et al.
2005/0171558 A1 8/2005 Abovitz et al.
2006/0100610 A1 5/2006 Wallace et al.
2006/0173329 A1 8/2006 Marquart et al.
2006/0184396 A1 8/2006 Dennis et al.
2006/0241416 A1 10/2006 Marquart et al.
2006/0291612 A1 12/2006 Nishide et al.
2007/0015987 A1 1/2007 Benlloch Baviera et al.
2007/0021738 A1 1/2007 Hasser et al.
2007/0038059 A1 2/2007 Sheffer et al.
2007/0073133 A1 3/2007 Schoenefeld
2007/0156121 A1 7/2007 Millman et al.
2007/0156157 A1 7/2007 Nahum et al.
2007/0167712 A1 7/2007 Keglovich et al.
2007/0233238 A1 10/2007 Huynh et al.
2008/0004523 A1 1/2008 Jensen
2008/0013809 A1 1/2008 Zhu et al.
2008/0033283 A1 2/2008 Dellaca et al.
2008/0046122 A1 2/2008 Manzo et al.
2008/0082109 A1 4/2008 Moll et al.
2008/0108912 A1 5/2008 Node-Langlois
2008/0108991 A1 5/2008 Von Jako
2008/0109012 A1 5/2008 Falco et al.
2008/0144906 A1 6/2008 Allred et al.
2008/0161680 A1 7/2008 Von Jako et al.
2008/0161682 A1 7/2008 Kendrick et al.
2008/0177203 A1 7/2008 von Jako
2008/0214922 A1 9/2008 Hartmann et al.
2008/0228068 A1 9/2008 Viswanathan et al.
2008/0228196 A1 9/2008 Wang et al.
2008/0235052 A1 9/2008 Node-Langlois et al.
2008/0269596 A1 10/2008 Revie et al.

(56) References Cited

U.S. PATENT DOCUMENTS

2008/0287771 A1 11/2008 Anderson
2008/0287781 A1 11/2008 Revie et al.
2008/0300477 A1 12/2008 Lloyd et al.
2008/0300478 A1 12/2008 Zuhars et al.
2008/0302950 A1 12/2008 Park et al.
2008/0306490 A1 12/2008 Lakin et al.
2008/0319311 A1 12/2008 Hamadeh
2009/0012509 A1 1/2009 Csavoy et al.
2009/0030428 A1 1/2009 Omori et al.
2009/0080737 A1 3/2009 Battle et al.
2009/0185655 A1 7/2009 Koken et al.
2009/0198121 A1 8/2009 Hoheisel
2009/0216113 A1 8/2009 Meier et al.
2009/0228019 A1 9/2009 Gross et al.
2009/0259123 A1 10/2009 Navab et al.
2009/0259230 A1 10/2009 Khadem et al.
2009/0264899 A1 10/2009 Appenrodt et al.
2009/0281417 A1 11/2009 Hartmann et al.
2010/0022874 A1 1/2010 Wang et al.
2010/0039506 A1 2/2010 Sarvestani et al.
2010/0125286 A1 5/2010 Wang et al.
2010/0130986 A1 5/2010 Mailloux et al.
2010/0228117 A1 9/2010 Hartmann
2010/0228265 A1 9/2010 Prisco
2010/0249571 A1 9/2010 Jensen et al.
2010/0274120 A1 10/2010 Heuscher
2010/0280363 A1 11/2010 Skarda et al.
2010/0331858 A1 12/2010 Simaan et al.
2011/0022229 A1 1/2011 Jang et al.
2011/0077504 A1 3/2011 Fischer et al.
2011/0098553 A1 4/2011 Robbins et al.
2011/0137152 A1 6/2011 Li
2011/0213384 A1 9/2011 Jeong
2011/0224684 A1 9/2011 Larkin et al.
2011/0224685 A1 9/2011 Larkin et al.
2011/0224686 A1 9/2011 Larkin et al.
2011/0224687 A1 9/2011 Larkin et al.
2011/0224688 A1 9/2011 Larkin et al.
2011/0224689 A1 9/2011 Larkin et al.
2011/0224825 A1 9/2011 Larkin et al.
2011/0230967 A1 9/2011 O'Halloran et al.
2011/0238080 A1 9/2011 Ranjit et al.
2011/0276058 A1 11/2011 Choi et al.
2011/0282189 A1 11/2011 Graumann
2011/0286573 A1 11/2011 Schretter et al.
2011/0295062 A1 12/2011 Gratacos Solsona et al.
2011/0295370 A1 12/2011 Suh et al.
2011/0306986 A1 12/2011 Lee et al.
2012/0035507 A1 2/2012 George et al.
2012/0046668 A1 2/2012 Gantes
2012/0051498 A1 3/2012 Koishi
2012/0053597 A1 3/2012 Anvari et al.
2012/0059248 A1 3/2012 Holsing et al.
2012/0071753 A1 3/2012 Hunter et al.
2012/0108954 A1 5/2012 Schulhauser et al.
2012/0136372 A1 5/2012 Amat Girbau et al.
2012/0143084 A1 6/2012 Shoham
2012/0184839 A1 7/2012 Woerlein
2012/0197182 A1 8/2012 Millman et al.
2012/0226145 A1 9/2012 Chang et al.
2012/0235909 A1 9/2012 Birkenbach et al.
2012/0245596 A1 9/2012 Meenink
2012/0253332 A1 10/2012 Moll
2012/0253360 A1 10/2012 White et al.
2012/0256092 A1 10/2012 Zingerman
2012/0294498 A1 11/2012 Popovic
2012/0296203 A1 11/2012 Hartmann et al.
2013/0006267 A1 1/2013 Odermatt et al.
2013/0016889 A1 1/2013 Myronenko et al.
2013/0030571 A1 1/2013 Ruiz Morales et al.
2013/0035583 A1 2/2013 Park et al.
2013/0060146 A1 3/2013 Yang et al.
2013/0060337 A1 3/2013 Petersheim et al.
2013/0094742 A1 4/2013 Feilkas
2013/0096574 A1 4/2013 Kang et al.
2013/0113791 A1 5/2013 Isaacs et al.
2013/0116706 A1 5/2013 Lee et al.
2013/0131695 A1 5/2013 Scarfogliero et al.
2013/0144307 A1 6/2013 Jeong et al.
2013/0158542 A1 6/2013 Manzo et al.
2013/0165937 A1 6/2013 Patwardhan
2013/0178867 A1 7/2013 Farritor et al.
2013/0178868 A1 7/2013 Roh
2013/0178870 A1 7/2013 Schena
2013/0204271 A1 8/2013 Brisson et al.
2013/0211419 A1 8/2013 Jensen
2013/0211420 A1 8/2013 Jensen
2013/0218142 A1 8/2013 Tuma et al.
2013/0223702 A1 8/2013 Holsing et al.
2013/0225942 A1 8/2013 Holsing et al.
2013/0225943 A1 8/2013 Holsing et al.
2013/0231556 A1 9/2013 Holsing et al.
2013/0237995 A1 9/2013 Lee et al.
2013/0245375 A1 9/2013 DiMaio et al.
2013/0261640 A1 10/2013 Kim et al.
2013/0272488 A1 10/2013 Bailey et al.
2013/0272489 A1 10/2013 Dickman et al.
2013/0274761 A1 10/2013 Devengenzo et al.
2013/0281821 A1 10/2013 Liu et al.
2013/0296884 A1 11/2013 Taylor et al.
2013/0303887 A1 11/2013 Holsing et al.
2013/0307955 A1 11/2013 Deitz et al.
2013/0317521 A1 11/2013 Choi et al.
2013/0325033 A1 12/2013 Schena et al.
2013/0325035 A1 12/2013 Hauck et al.
2013/0331686 A1 12/2013 Freysinger et al.
2013/0331858 A1 12/2013 Devengenzo et al.
2013/0331861 A1 12/2013 Yoon
2013/0342578 A1 12/2013 Isaacs
2013/0345717 A1 12/2013 Markvicka et al.
2013/0345757 A1 12/2013 Stad
2014/0001235 A1 1/2014 Shelton, IV
2014/0012131 A1 1/2014 Heruth et al.
2014/0031664 A1 1/2014 Kang et al.
2014/0046128 A1 2/2014 Lee et al.
2014/0046132 A1 2/2014 Hoeg et al.
2014/0046340 A1 2/2014 Wilson et al.
2014/0049629 A1 2/2014 Siewerdsen et al.
2014/0058406 A1 2/2014 Tsekos
2014/0073914 A1 3/2014 Lavallee et al.
2014/0080086 A1 3/2014 Chen
2014/0081128 A1 3/2014 Verard et al.
2014/0088612 A1 3/2014 Bartol et al.
2014/0094694 A1 4/2014 Moctezuma de la Barrera
2014/0094851 A1 4/2014 Gordon
2014/0096369 A1 4/2014 Matsumoto et al.
2014/0100587 A1 4/2014 Farritor et al.
2014/0121676 A1 5/2014 Kostrzewski et al.
2014/0128882 A1 5/2014 Kwak et al.
2014/0130810 A1 5/2014 Azizian et al.
2014/0135796 A1 5/2014 Simon et al.
2014/0142591 A1 5/2014 Alvarez et al.
2014/0142592 A1 5/2014 Moon et al.
2014/0148692 A1 5/2014 Hartmann et al.
2014/0163581 A1 6/2014 Devengenzo et al.
2014/0171781 A1 6/2014 Stiles
2014/0171900 A1 6/2014 Stiles
2014/0171965 A1 6/2014 Loh et al.
2014/0180308 A1 6/2014 von Grunberg
2014/0180309 A1 6/2014 Seeber et al.
2014/0187915 A1 7/2014 Yaroshenko et al.
2014/0188132 A1 7/2014 Kang
2014/0194699 A1 7/2014 Roh et al.
2014/0221819 A1 8/2014 Sarment
2014/0222023 A1 8/2014 Kim et al.
2014/0228631 A1 8/2014 Kwak et al.
2014/0234804 A1 8/2014 Huang et al.
2014/0257328 A1 9/2014 Kim et al.
2014/0257329 A1 9/2014 Jang et al.
2014/0257330 A1 9/2014 Choi et al.
2014/0275760 A1 9/2014 Lee et al.
2014/0275985 A1 9/2014 Walker et al.
2014/0276931 A1 9/2014 Parihar et al.
2014/0276940 A1 9/2014 Seo

(56) References Cited

U.S. PATENT DOCUMENTS

| | | | |
|---|---|---|---|
| 2014/0276944 | A1 | 9/2014 | Farritor et al. |
| 2014/0288413 | A1 | 9/2014 | Hwang et al. |
| 2014/0299648 | A1 | 10/2014 | Shelton, IV et al. |
| 2014/0303434 | A1 | 10/2014 | Farritor et al. |
| 2014/0303643 | A1 | 10/2014 | Ha et al. |
| 2014/0305995 | A1 | 10/2014 | Shelton, IV et al. |
| 2014/0309659 | A1 | 10/2014 | Roh et al. |
| 2014/0316436 | A1 | 10/2014 | Bar et al. |
| 2014/0323803 | A1 | 10/2014 | Hoffman et al. |
| 2014/0324070 | A1 | 10/2014 | Min et al. |
| 2014/0330288 | A1 | 11/2014 | Date et al. |
| 2014/0364720 | A1 | 12/2014 | Darrow et al. |
| 2014/0371577 | A1 | 12/2014 | Maillet et al. |
| 2015/0039034 | A1 | 2/2015 | Frankel et al. |
| 2015/0085970 | A1 | 3/2015 | Bouhnik et al. |
| 2015/0146847 | A1 | 5/2015 | Liu |
| 2015/0150524 | A1 | 6/2015 | Yorkston et al. |
| 2015/0196261 | A1 | 7/2015 | Funk |
| 2015/0213633 | A1 | 7/2015 | Chang et al. |
| 2015/0335480 | A1 | 11/2015 | Alvarez et al. |
| 2015/0342647 | A1 | 12/2015 | Frankel et al. |
| 2016/0005194 | A1 | 1/2016 | Schretter et al. |
| 2016/0166329 | A1 | 6/2016 | Langan et al. |
| 2016/0235480 | A1 | 8/2016 | Scholl et al. |
| 2016/0249990 | A1 | 9/2016 | Glozman et al. |
| 2016/0302871 | A1 | 10/2016 | Gregerson et al. |
| 2016/0320322 | A1 | 11/2016 | Suzuki |
| 2016/0331335 | A1 | 11/2016 | Gregerson et al. |
| 2017/0135770 | A1 | 5/2017 | Scholl et al. |
| 2017/0143284 | A1 | 5/2017 | Sehnert et al. |
| 2017/0143426 | A1 | 5/2017 | Isaacs et al. |
| 2017/0156816 | A1 | 6/2017 | Ibrahim |
| 2017/0202629 | A1 | 7/2017 | Maillet et al. |
| 2017/0212723 | A1 | 7/2017 | Atarot et al. |
| 2017/0215825 | A1 | 8/2017 | Johnson et al. |
| 2017/0215826 | A1 | 8/2017 | Johnson et al. |
| 2017/0215827 | A1 | 8/2017 | Johnson et al. |
| 2017/0231710 | A1 | 8/2017 | Scholl et al. |
| 2017/0258426 | A1 | 9/2017 | Risher-Kelly et al. |
| 2017/0273748 | A1 | 9/2017 | Hourtash et al. |
| 2017/0296277 | A1 | 10/2017 | Hourtash et al. |
| 2017/0360493 | A1 | 12/2017 | Zucher et al. |
| 2019/0060556 | A1 * | 2/2019 | Huiszoon .............. A61M 5/001 |
| 2024/0148328 | A1 * | 5/2024 | Fedon .................. A61B 5/0538 |

OTHER PUBLICATIONS

V. Makarovaite, etc. "Passive UHF RFID Voice Prosthesis Mounted Sensor for Microbial Growth Detection," in IEEE Journal of Radio Frequency Identification, vol. 4, No. 4, pp. 384-390, Dec. 2020 (Year: 2020).*

* cited by examiner

IMPLANTABLE RF SENSOR FOR BIOFILM DETECTION

FIELD

The present disclosure relates to medical implants, including joint arthroplasty.

BACKGROUND

Periprosthetic joint infection (PJI) is one of the most feared complications in joint arthroplasty due to the ineffectiveness of antibiotics, invasive treatment options, and relatively high annual mortality rate of 4%. If caught early enough, antibiotics and natural immune responses are very effective at intercepting the free-floating bacteria within the surgical site. However, antibiotics are remarkably ineffective at eradicating bacteria within biofilm on the surface of the implant.

Biofilm develops as bacteria adhere to and colonize on the surface of an implant. The biofilm layer serves as a biochemical fortress that prevents penetration of antibiotic agents. It has been reported that 500-5000 times the concentration of antibiotics are required to have the same effectiveness on biofilm bacteria as compared to free-floating planktonic bacteria. As a result, the most common treatment for PJI is highly invasive two-stage revision.

Two-stage revision involves an initial operation to remove the septic implant and debride the surgical site and a second procedure to place new implant components. Although two-stage revision is the most common treatment option for PJI, the success rate has been reported to be only 85%. In addition, the risk of reinfection following revision for PJI has been reported to be 9% compared to 1-2% following the primary procedure. Also, the annual mortality rate has been reported to be as high as 14% following two-stage revision.

SUMMARY

Embodiments of the present disclosure are directed to smart joint reconstruction implants that can provide physicians/clinicians and their patients the ability to monitor, detect, and diagnose PJI.

Some embodiments of the present disclosure are directed to a medical implant that includes an implant component configured to be implanted in a patient, a radio frequency (RF) transmit antenna in the implant component and configured to transmit a RF signal, and circuitry within the implant component. The circuitry is operative to generate the RF signal to the RF transmit antenna, determine a characteristic of attenuation of the RF signal when the RF transmit antenna is transmitting the RF signal while implanted in the patient, and detect presence of biofilm on the medical implant based on the characteristic of attenuation of the RF signal.

Possible advantages that may be provided by one or one of these and other embodiments disclosed herein may include early monitoring of a formation of biofilm to provide early detection of PJI and feedback on the effectiveness of treatment. Additionally, the embodiment(s) may provide sensing and/or control elements integrated within the tibial insert. These sensing and/or control elements may provide the benefit(s) of no additional components on the surface of the implant exposed to synovial fluid and tissue and greater reliability.

Other medical implants and corresponding methods according to embodiments of the present disclosure will be or become apparent to one with skill in the art upon review of the following drawings and detailed description. It is intended that all such additional medical implants and methods be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings.

DETAILED DESCRIPTION

Figure 1:
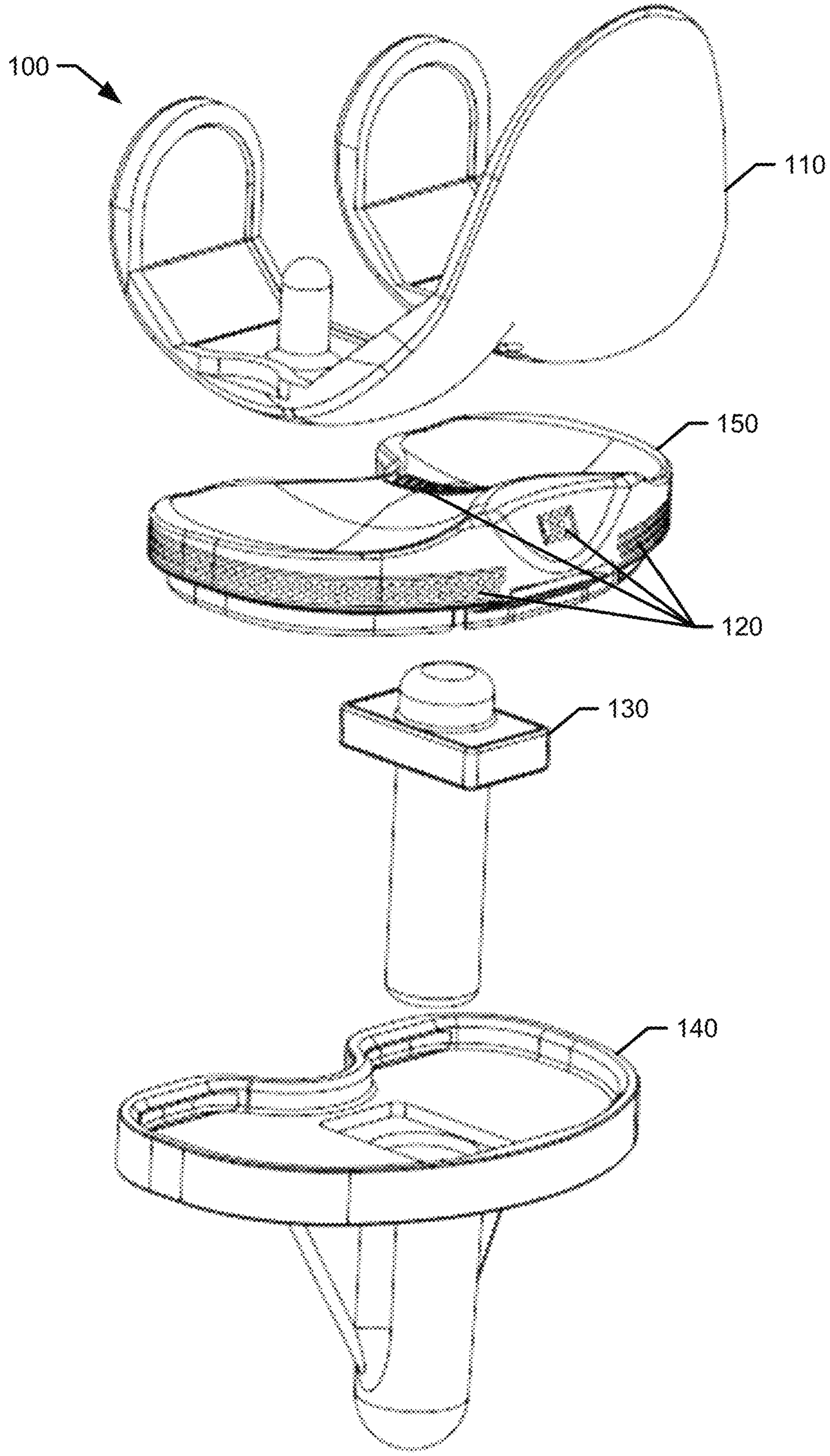
FIG. 1 illustrates an exploded isometric view of some components of a medical implant including a femoral component, tibial insert, energy storage device, and tibial tray according to some embodiments of the present disclosure.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Some embodiments of the present disclosure are directed to joint reconstruction implants that have electronic circuits ("smart implants") which operate to provide physicians and/or their patients the operational ability to monitor, detect, and diagnose Periprosthetic Joint Infection (PJI). The smart implant may include an implantable RF sensor (e.g., a RF antenna) capable of detecting bacterial biofilm on the surface of implant components.

Post-operatively, the smart implant may sense the presence of biofilm on the surface of implant components and transmit the sensor readings to a clinician. The clinician may decide on treatment based on the sensor readings, information provided to the clinician through an accompanying patient engagement mobile app, and direct consultation. If the clinician determines that the patient has developed or is likely to develop an infection, they may more closely monitor the patient and intervene with antibiotics or surgical debridement.

FIG. 1 illustrates an exploded isometric view of some components of a medical implant 100 including a femoral component 110, tibial insert 150, energy storage device 130, and tibial tray 140 according to some embodiments of the present disclosure.

Referring to FIG. 1, medical implant 100 is a knee replacement implant. The tibial insert 150 may be housed between the tibial tray 140 and femoral component 110 within cavities in each component. FIG. 1 is an implant construct for total knee arthroplasty, however, it should be noted that the present disclosure is directed to various embodiments in any orthopedic implant application including but not limited to partial knee arthroplasty, revision knee arthroplasty, total hip arthroplasty, intramedullary nailing, trauma plating, and spinal fusion.

The tibial insert 150 of the medical implant 100 may include at least one RF antenna (e.g., plurality of RF antennas 120) that is exposed to or shielded from (e.g., RF window discussed below) fluid and/or tissue of a patient that the medical implant 100 is implanted in. For example, the tibial insert 150 includes two sets of RF antennas in sides of the tibial insert 150, a third set of RF antennas in a top of the tibial insert 150 that is facing upward, and a fourth set of RF antennas that is in a front of the tibial insert 150 and is facing in a tilted forward facing direction. While embodiments illustrate and describe specific placements of the one or more RF antennas, embodiments herein are not limited to such placements and can be in any surface of the medical implant 100 such as the tibial insert 150, femoral component 110, and/or tibial tray 140. The femoral component 110, tibial insert 150, and tibial tray 140 may generally be referred to herein as an implant component.

In some preferred embodiments, the RF antennas are placed in locations where there is minimal or no articulating wear from the different components of the medical implant. For example, in locations where the different components of the medical implant do not contact each other while implanted in the patient. However, since the RF antenna(s) are in the medical implant 100 and can be protected by a RF window (discussed more below), the RF antenna(s) may be in locations where this is articular wear from the different components of the medical implant.

In additional or alternative embodiments, the RF antennas are placed in locations where biofilm is more likely to form on the medical implant 100.

Figure 2A:
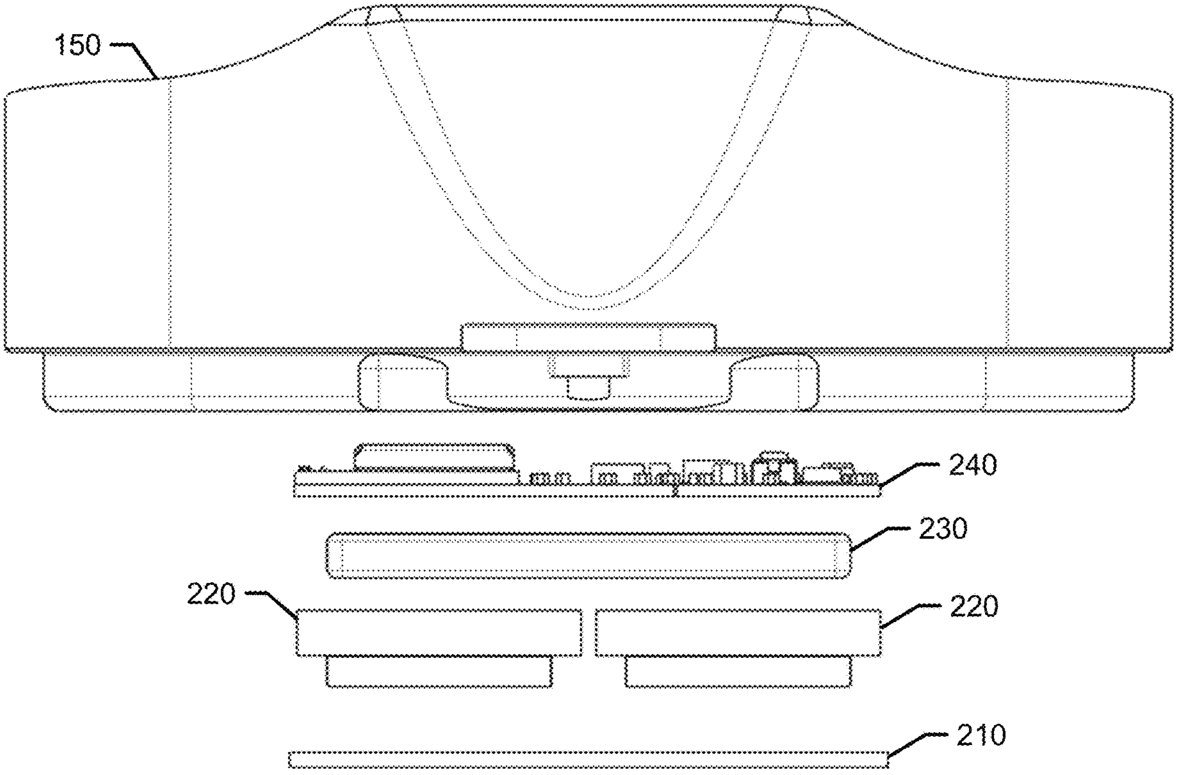
FIG. 2A illustrates a side exploded view of the tibial insert with an integrated RF-based biofilm sensor with laterally spaced transmission (Tx) and reception (Rx) antennas, according to some embodiments of the present disclosure.

FIG. 2A illustrates a side exploded view of the tibial insert 150 with an integrated RF-based biofilm sensor with laterally spaced transmission (Tx) and reception (Rx) antennas (e.g., RF antennas 220 which may include a RF transmit antenna and a RF receive antenna), according to some embodiments of the present disclosure. The term "RF antenna" can correspond to an antenna that is configured to resonate when excited with a transmit/receive signal in a defined RF frequency range.

It should be noted that while one RF transmit antenna and one RF receive antenna is illustrated herein, more than one RF transmit antenna and more than one RF receive antenna may be used. Additionally, in some embodiments, the RF receive antenna is optional as will be below.

In some embodiments, sets of RF transmit antennas and RF receive antennas are located in different locations in the medical implant and are used to monitor and detect the presence of biofilm at the corresponding different locations on the medical implant. In some embodiments, the sets comprise one or more RF transmit antennas and one or more RF receive antennas. In additional or alternative embodiments, the sets comprise more than one RF transmit antenna and one RF receive antenna, or vice versa.

Figure 2B:
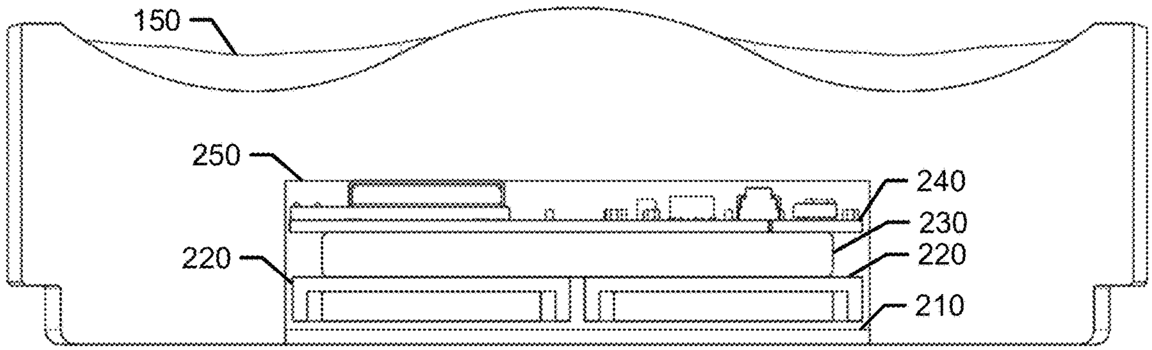
FIG. 2B illustrates a side sectional view of the tibial insert with an integrated RF-based biofilm sensor with laterally spaced Tx and Rx antennas, according to some embodiments of the present disclosure.

FIG. 2B illustrates a side sectional view of the tibial insert 150 with the integrated RF-based biofilm sensor with laterally spaced Tx and Rx antennas (e.g., the RF antennas 220), according to some embodiments of the present disclosure.

The tibial insert 150 may include a RF window 210 that extends across the RF transmit antenna and the RF receive antenna (e.g., RF based antennas 220) and separates the antennas from fluid and/or tissue while the medical implant is implanted in the patient. The RF window 210 may be a layer that comprises the same material or a different material than an adjacent surface of the medical implant. In some embodiments, the RF window 210 and the medical implant comprise of a RF-transparent material. In some embodiments, the RF window 210 hermetically seals the RF based antennas 220 within a housing 250 in the tibial insert 150.

The RF based antennas 220 may be substantially shielded from each other by electromagnetic field (EMF) shielding to reduce or prevent a shortest distance (direct) signal pathway therebetween (discussed in more detail below).

Biofilm typically forms non-uniformly in one or more spots on the surface of the medical implant where planktonic bacterial attachment is preferential due to surface roughness or other factors. In some embodiments, the RF window could be intentionally designed to serve as the preferential attachment surface for planktonic bacteria, thereby increasing the probability that a biofilm forms on the RF window rather than a non-instrumented portion of the medical implant surface. For example, the RF window may include a rougher surface, exposed to the patient (e.g., fluid and/or tissue of the patient), than an adjacent surface of the implant component (e.g., tibial insert 150 of FIG. 2A) exposed to the patient to promote earlier formation of biofilm on the rougher surface of the RF window. Alternatively or additionally, an external surface of the RF window may be covered with a material that promotes earlier formation of biofilm.

The tibial insert 150 further includes an energy storage device 230, e.g., rechargeable battery or capacitive circuitry, that is additional to or alternative of the energy storage device 130. In some embodiments, the energy storage device 230 may be configured to power the circuitry 240 within the tibial insert 150 and/or the RF antennas 220 within the tibial insert 150. In other embodiments, circuitry 240 is powered primarily or fully by the energy storage device 130 of FIG. 1. In embodiments where the energy storage device 130 is the primary source of power, the energy storage device 230 acts as secondary or back-up power source.

Circuitry 240 may include one or more processor circuits ("processor") which execute instructions stored in one or more memory circuits ("memory"), and/or application specific integrated circuit(s) which perform defined logical operations. The circuitry further includes RF amplifier(s) and transmitter circuits, and may include a RF receiver circuits.

In some embodiments, the RF antennas 220 are electrically connected to the energy storage device (e.g., energy storage device 130 and/or energy storage device 230) through insulated electrical traces or wires routed on the surface of the tibial insert 150 or through the body of the tibial insert 150. The electrical traces or wires may terminate at connectors that interface with pass-through connectors of the tibial insert 150. The housing 250 of the tibial insert 150 (along with other parts of the medical implant) may be constructed at least in part of a material that minimizes RF interference. In some embodiment, the top portions of the housing are constructed of a RF transparent material such as PEEK (polyetheretherketone) to allow transmission of the radio waves. In some embodiments, the bottom component of the housing could be constructed of a RF transparent material such as PEEK or a RF shielding material such as TAV (titanium).

In some embodiments, circuitry 240 is a printed circuit assembly (PCA). The PCA may include electronic components and circuitry required for communication, wireless charging, sensing, including the RF antenna(s).

As shown in FIG. 2B, in some embodiments, the RF based antennas 220 (e.g., RF transmit antenna and/or the RF receive antenna), the energy storage device 230, and circuitry 240 are recessed in the implant component (e.g., tibial insert 150). Housing 250 along with the RF window may support these components within the medical implant.

Figure 3A:
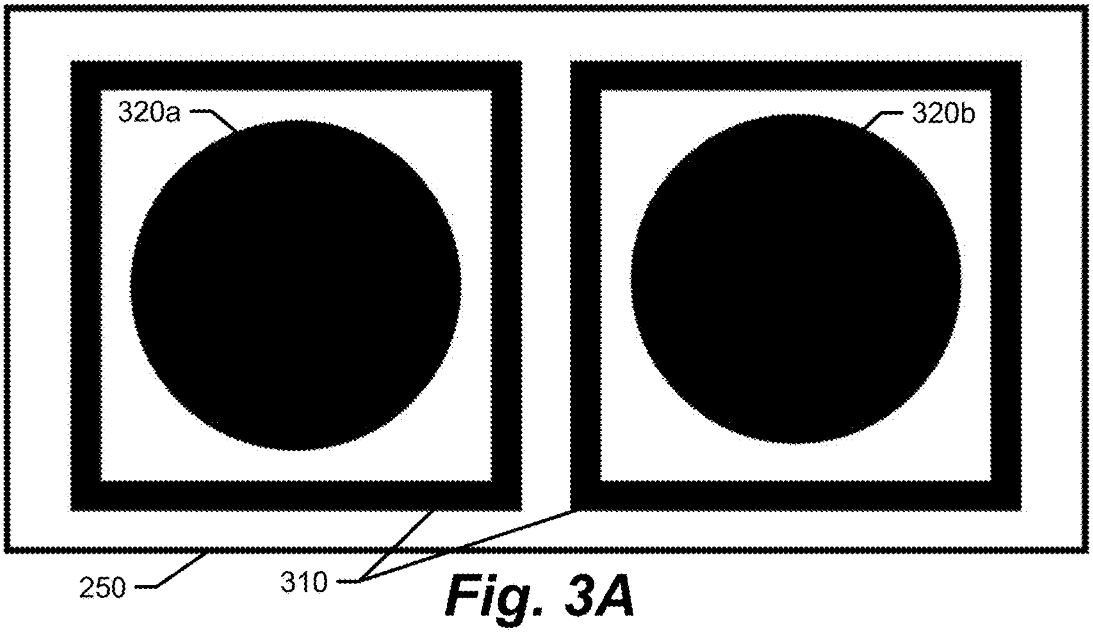
FIG. 3A illustrates a top view of a RF-based biofilm sensor with laterally spaced Tx and Rx antennas, according to some embodiments of the present disclosure.

FIG. 3A illustrates a top view of a RF-based biofilm sensor with laterally spaced Tx and Rx antennas, according to some embodiments of the present disclosure.

The laterally spaced Tx and Rx antennas may include at least one RF transmit antenna 320*a* and at least one RF transmit antenna 320*b*.

The RF transmit antenna 320*a* may be in (at least partially within) the implant component (e.g., a tibial insert 150) and configured to transmit a RF signal. The RF receive antenna 320*b* may be in the implant component (e.g., a tibial insert 150) and configured to receive the RF signal.

The housing 250 of the tibial insert 150 may include EMF shielding 310 positioned between the RF transmit antenna 320*a* and the RF receive antenna 320*b* and configured to attenuate RF signaling along a direct pathway from the RF transmit antenna 320*a* to the RF receive antenna 320*b* through the EMF shielding.

Figure 3B:
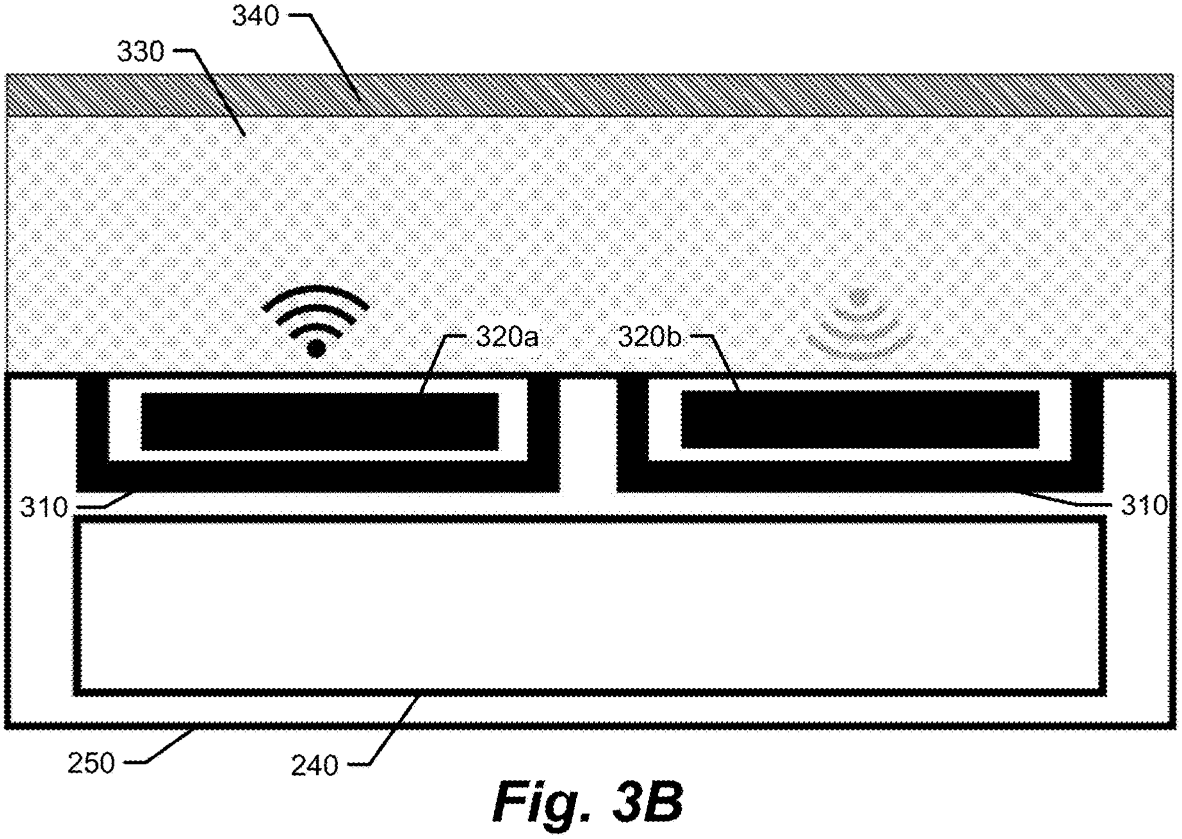
FIG. 3B illustrates a side sectional view of a RF-based biofilm sensor with laterally spaced Tx and Rx antennas, according to some embodiments of the present disclosure.

FIG. 3B illustrates a side sectional view of a RF-based biofilm sensor with laterally spaced Tx and Rx antennas, according to some embodiments of the present disclosure.

In some embodiments, the medical implant includes an implant component (e.g., tibial insert 150) configured to be implanted in a patient, a RF transmit antenna 320*a* in the implant component and configured to transmit a RF signal, and circuitry 240 within the implant component that is operative to generate a RF signal to the RF transmit antenna 320*a*. The circuitry is further operative to determine a characteristic of attenuation of the RF signal when the RF transmit antenna 320*a* is transmitting the RF signal while implanted in the patient. The circuitry is further operative to detect presence of biofilm based on the characteristic of attenuation of the RF signal.

In some embodiments, the characteristic of attenuation of the RF signal is determined based on the reflected power of the RF signal provided by the circuitry 240 toward the RF transmit antenna 320*a*. For these operations, the characteristic of attenuation may be detected without necessarily including a receive antenna and coupled receive circuitry.

In some embodiments, the medical implant further includes a RF receive antenna 320*n* in the implant component and configured to receive the RF signal. In these embodiments, the characteristic of attenuation of the RF signal is determined based on the RF signal characteristics received at the RF receive antenna. The RF signal is transmitted by the RF transmit antenna 320*a* and travels through fluid 330 and/or tissue 340 of the patient and is received by the RF receive antenna 320*b*. Then circuitry 240 determines a characteristic of attenuation of the RF signal based on the RF signal characteristics received at the RF receive antenna.

In some embodiments, the RF transmit antenna 320*a* and the RF receive antenna 320*b* are physically spaced apart from each other along a surface of the medical implant.

In some embodiments, the characteristic of attenuation of the RF signal is determined based on at least one of reflected power of the RF signal provided by the circuitry 240 toward the RF transmit antenna 320*a*, power transferred by the RF signal from the RF transmit antenna 320*a* to a RF receive antenna 320*b* in the implant component (e.g., tibial insert 150) and configured to receive the RF signal, a change in frequency between the RF signal transmitted by the RF transmit antenna 320*a* and the RF signal received by the RF receive antenna 320*b*, and a change in amplitude between the RF signal transmitted by the RF transmit antenna 320*a* and the RF signal received by the RF receive antenna 320*b*, a change in phase between the RF signal transmitted by the RF transmit antenna 320*a* and the RF signal received by the RF receive antenna 320*b*.

Figure 3C:
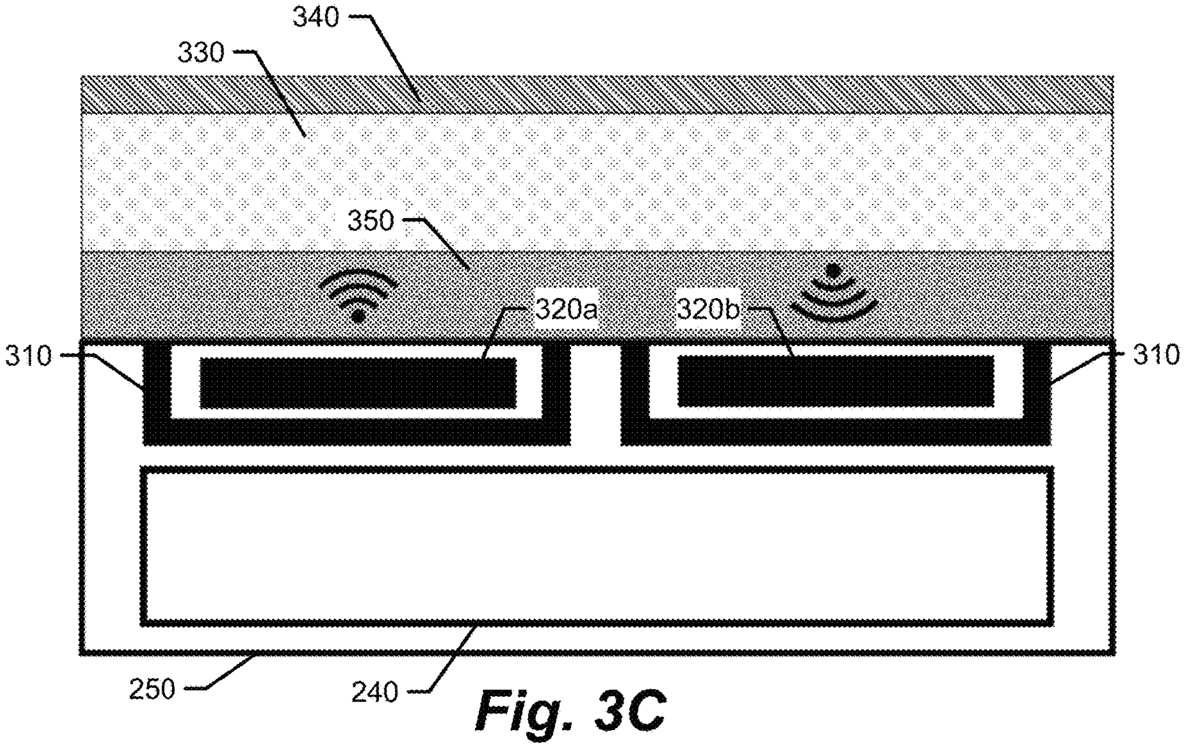
FIG. 3C illustrates a side sectional view of a RF-based biofilm sensor with laterally spaced Tx and Rx antennas according to some embodiments of the present disclosure, and with biofilm present.

FIG. 3C illustrates a side sectional view of a RF-based biofilm sensor with laterally spaced Tx and Rx antennas (e.g., RF transmit antenna 320*a* and RF receive antenna 320*b*) according to some embodiments of the present disclosure, and with biofilm 350 present.

In some embodiments, the detection of the presence of biofilm 350 comprises comparing the determined characteristic of attenuation of the RF signal to a threshold characteristic of attenuation defined based on a calibration measurement operation. For example, the characteristic(s) of attenuation could be compared to previously determined characteristic(s) of attenuation that were measured during a calibration measurement operation that occurred a period of time after the medical implant was implanted into the patient. In preferred embodiments, the calibration measurement operation would occur a short period after implantation into the patient to help ensure that biofilm has not already built up on the medical implant.

In some embodiments, the detection of the presence of biofilm comprises comparing the characteristic of attenuation of the RF signal to at least one prior characteristic of attenuation, and determining that biofilm is present based on the characteristic of attenuation of the RF signal being a threshold difference than the prior characteristic of attenuation. For example, if a characteristic of attenuation is determined to be a threshold difference than a previously determined characteristic of attenuation, then this may indicate the presence of biofilm on the medical implant, likely on a surface of the medical implant near the RF transmit antenna and/or the RF receive antenna.

Figure 3D:
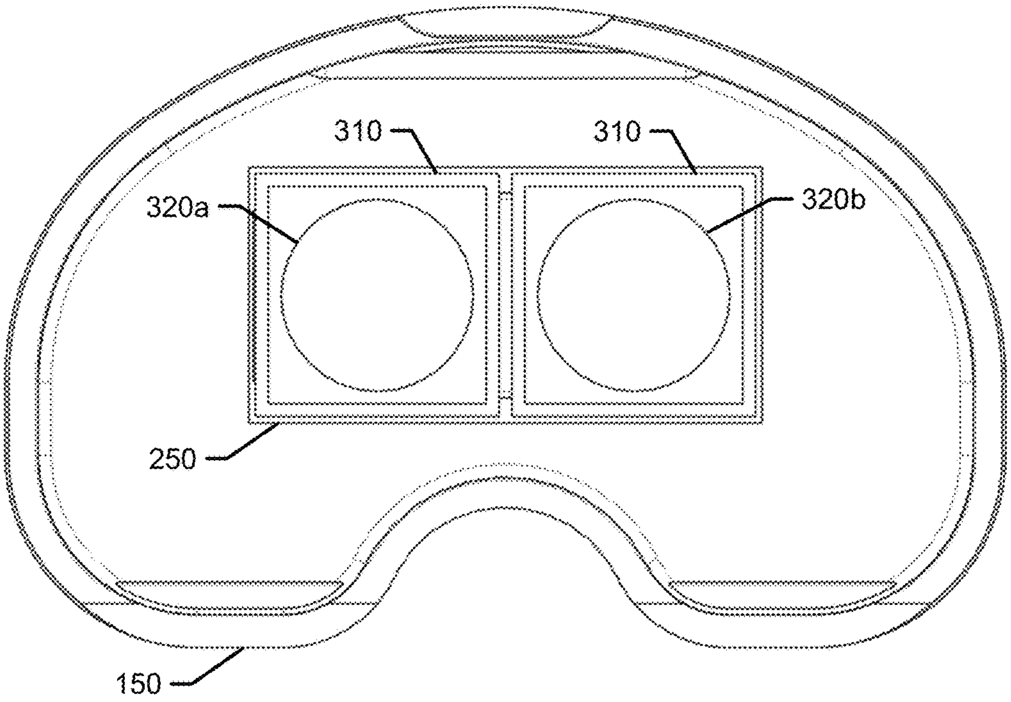
FIG. 3D illustrates a bottom view of the tibial insert with an integrated RF-based biofilm sensor with laterally spaced Tx and Rx antennas, according to some embodiments of the present disclosure.

FIG. 3D illustrates a bottom view of the tibial insert 150 with an integrated RF-based biofilm sensor with laterally spaced Tx and Rx antennas (e.g., RF transmit antenna 320*a* and RF receive antenna 320*b*), according to some embodiments of the present disclosure. In some embodiments, the RF transmit antenna 320*a* transmits signals out of the bottom of the tibial insert 150 to monitor and detect presence of biofilm on the bottom of the tibial insert 150.

Figure 4A:
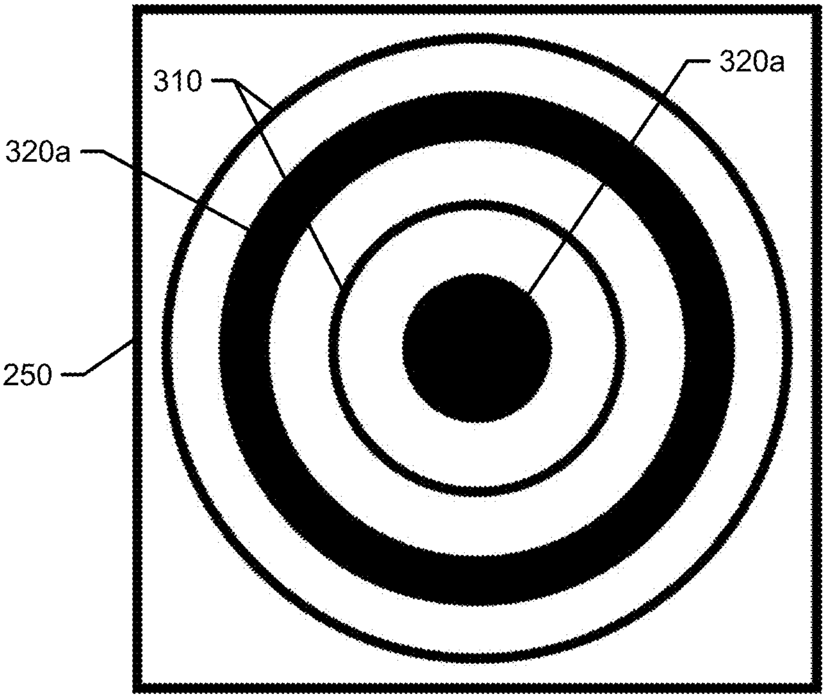
FIG. 4A illustrates a top view of a RF-based biofilm sensor with coaxial Tx and Rx antennas, according to some embodiments of the present disclosure.

FIG. 4A illustrates a top view of a RF-based biofilm sensor with coaxial Tx and Rx antennas (e.g., RF transmit antenna 320*a* and RF receive antenna 320*b*), according to some embodiments of the present disclosure.

In some embodiments, the RF transmit antenna 320*a* and RF receive antenna 320*b* are circular shaped and arranged concentrically with different diameters. For example, the RF transmit antenna 320*a* and RF receive antenna 320*b* may be coaxial and housed within the housing 250 in the tibial insert. In some embodiments, the housing 250 and/or implant component includes EMF shielding 310 positioned between the RF transmit antenna 320*a* and the RF receive antenna 320*b* and configured to attenuate RF signaling along a direct pathway from the RF transmit antenna 320*a* to the RF receive antenna 320*b* through the EMF shielding. The EMF shielding 310 may help to prevent the RF signal from being transmitted directly from the RF transmit antenna 320*a* to the RF receive antenna 320*b*, and may force the RF signal to travel through fluid 330 and or tissue 340 of the patient.

Concentrically is used herein to refer to one antenna being encircled by another antenna but which may or may not be coaxially aligned therewith.

Figure 4B:
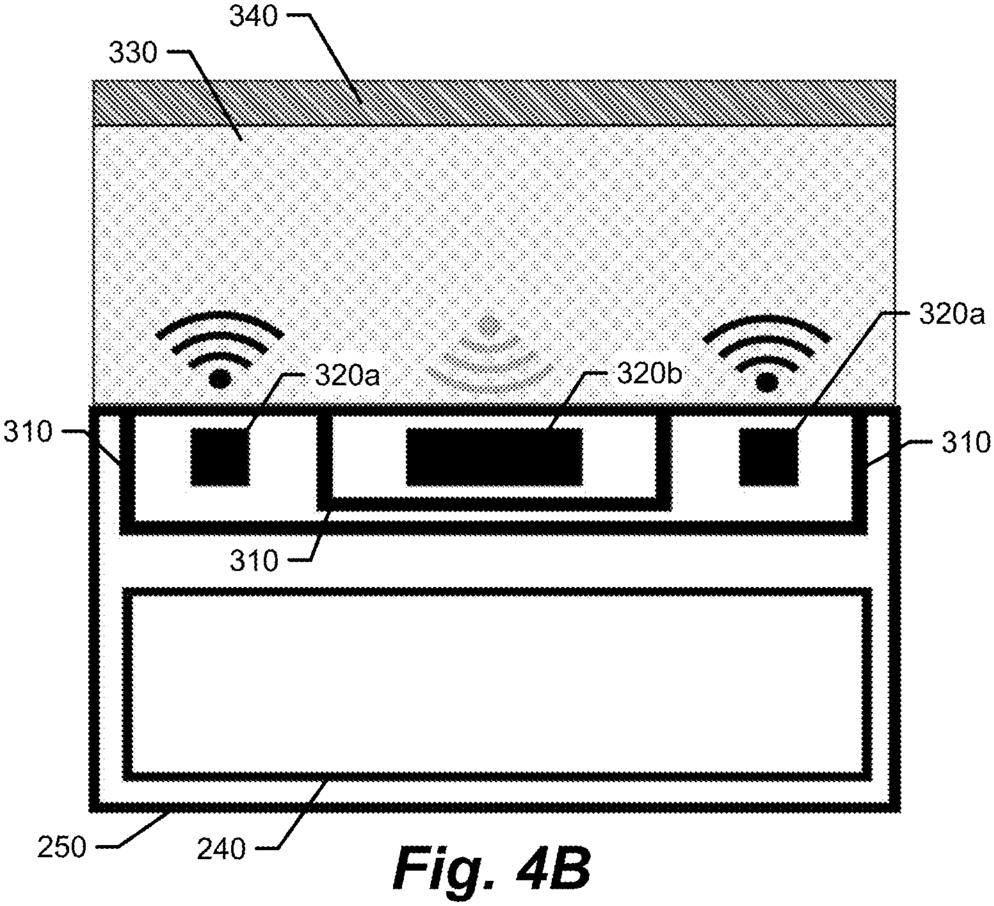
FIG. 4B illustrates a side sectional view of a RF-based biofilm sensor with coaxial Tx and Rx antennas, according to some embodiments of the present disclosure.

FIG. 4B illustrates a side sectional view of a RF-based biofilm sensor with coaxial Tx and Rx antennas (e.g., RF transmit antenna 320*a* and RF receive antenna 320*b*), according to some embodiments of the present disclosure. FIG. 4B is similar to FIG. 3B, except the RF transmit antenna 320*a* and RF receive antenna are circular shaped and arranged concentrically with different diameters. The RF transmit antenna 320*a* may transmit RF signal(s) and the RF receive antenna 320*b* may receive the RF signal(s) after the RF signal travels through fluid 330 and/or tissue 340 of a patient that the medical implant is implanted in.

Figure 4C:
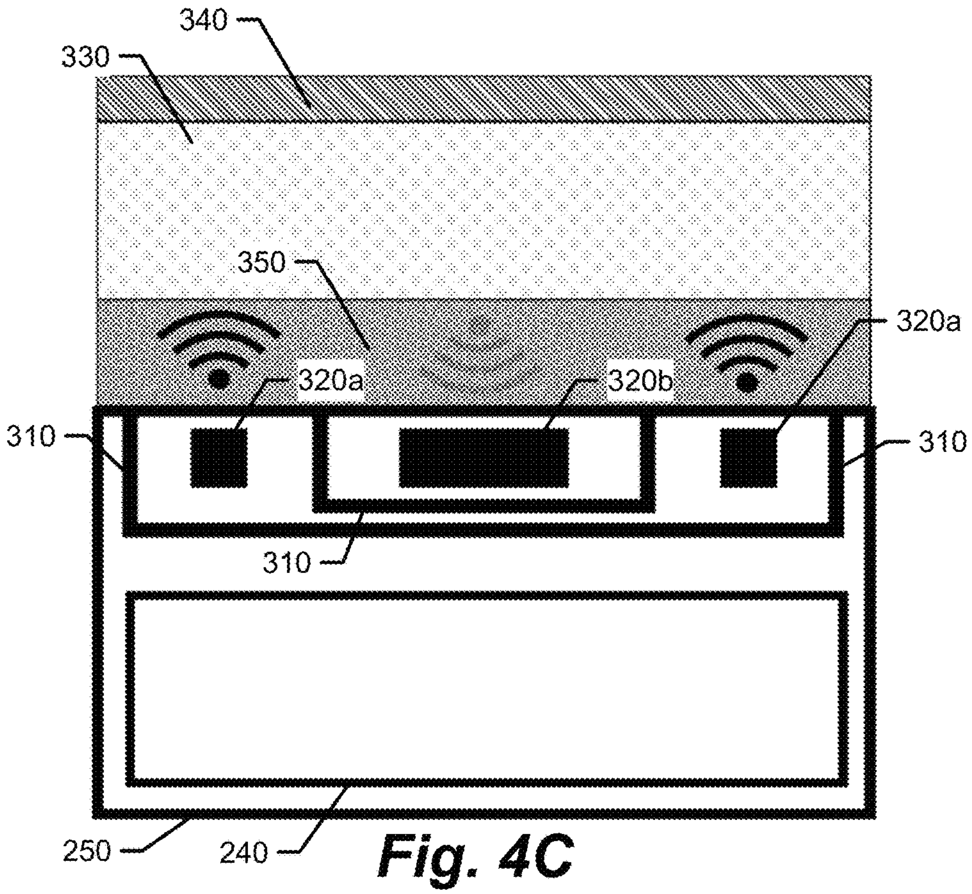
FIG. 4C illustrates a side sectional view of a RF-based biofilm sensor with coaxial Tx and Rx antennas according to some embodiments of the present disclosure, and with biofilm present.

FIG. 4C illustrates a side sectional view of a RF-based biofilm sensor with coaxial Tx and Rx antennas (e.g., RF transmit antenna 320*a* and RF receive antenna 320*b*) according to some embodiments of the present disclosure, and with biofilm present.

Figure 4D:
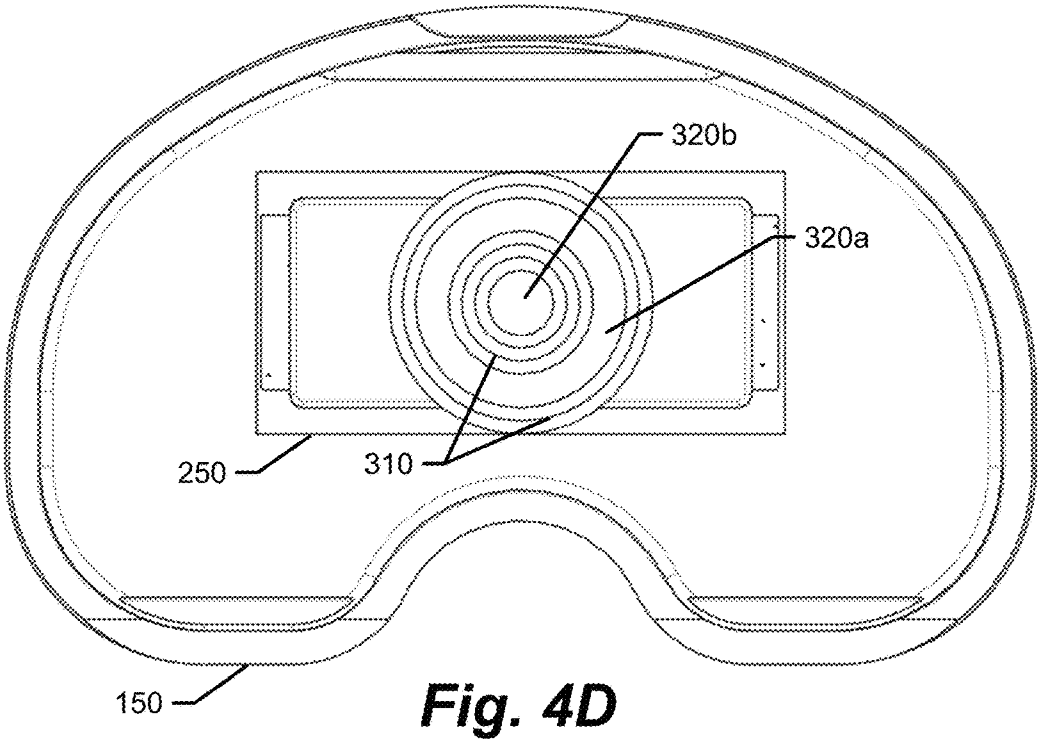
FIG. 4D illustrates a bottom view of the tibial insert with an integrated RF-based biofilm sensor with coaxial Tx and Rx antennas, according to some embodiments of the present disclosure.

FIG. 4D illustrates a bottom view of the tibial insert with an integrated RF-based biofilm sensor with coaxial Tx and Rx antennas, according to some embodiments of the present disclosure.

Figure 5A:
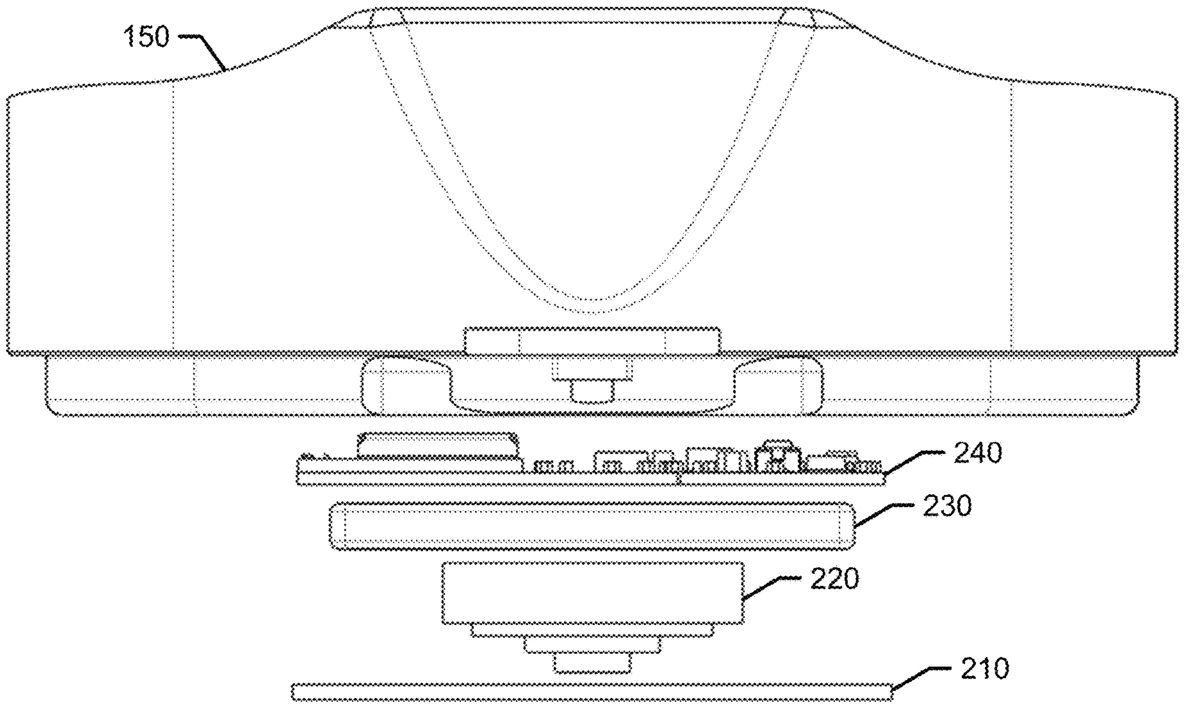
FIG. 5A illustrates a side sectional view of the tibial insert with an integrated RF-based biofilm sensor with coaxial Tx and Rx antennas, according to some embodiments of the present disclosure.

FIG. 5A illustrates a side sectional view of the tibial insert with an integrated RF-based biofilm sensor with coaxial Tx and Rx antennas (e.g., RF based antennas 220), according to some embodiments of the present disclosure.

Figure 5B:
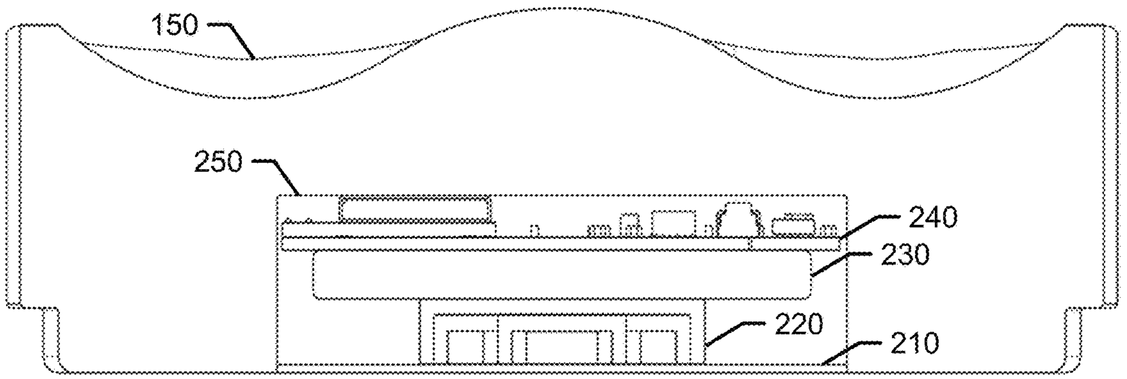
FIG. 5B illustrates a side exploded view of the tibial insert with an integrated RF-based biofilm sensor with coaxial Tx and Rx antennas, according to some embodiments of the present disclosure.

FIG. 5B illustrates a side exploded view of the tibial insert with an integrated RF-based biofilm sensor with coaxial Tx and Rx antennas (e.g., RF based antennas 220), according to some embodiments of the present disclosure.

Figure 6A:
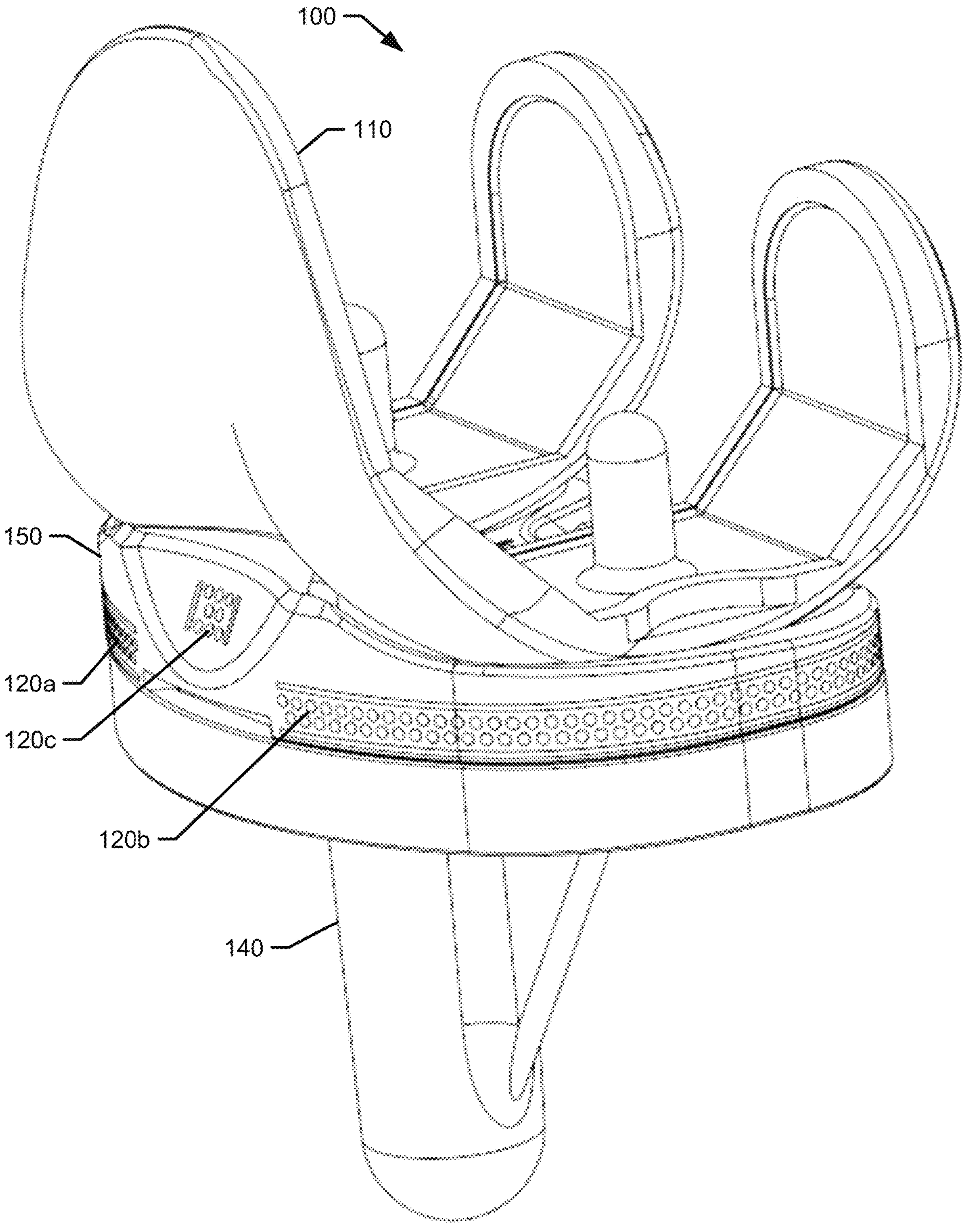
FIG. 6A illustrates another view of the medical implant with sets of RF-based biofilm sensors on either side of the tibial insert and another set of RF-based biofilm sensors centrally located on a frontward face of the tibial insert, according to some embodiments of the present disclosure.

FIG. 6A illustrates another view of the medical implant 100 with sets of RF-based biofilm sensors 120*a-b* on either side of the tibial insert 150 and another set of RF-based biofilm sensors 120*c* centrally located on a frontward (sideward) face of the tibial insert 150, according to some embodiments of the present disclosure.

Figure 6B:
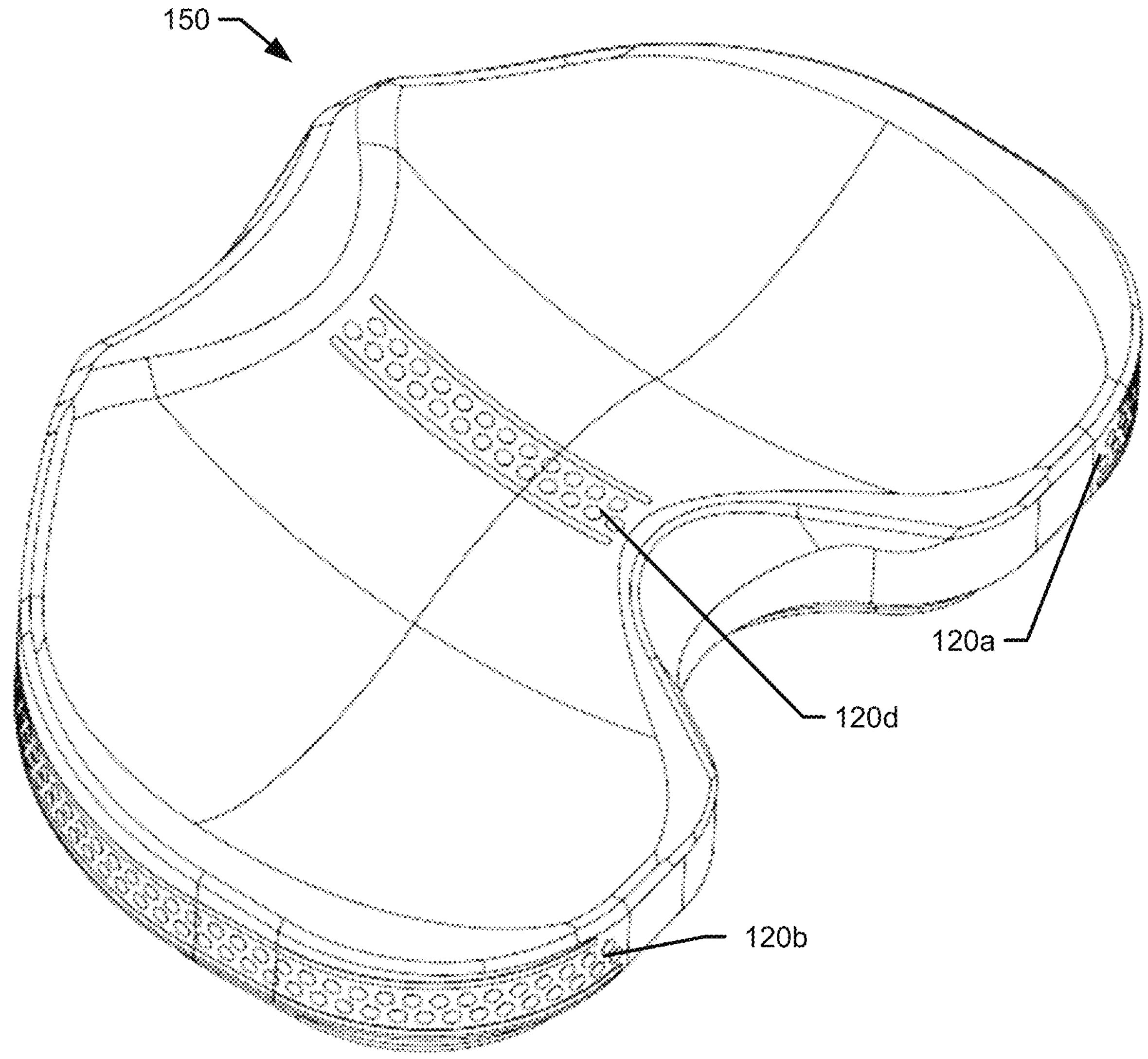
FIG. 6B illustrates yet another view of the tibial insert with two sets of RF-based biofilm sensors on either side of the tibial insert and a third sets of RF-based biofilm sensors centrally located on a top of the tibial insert, according to some embodiments of the present disclosure.

FIG. 6B illustrates yet another view of the tibial insert 150 with two sets of RF-based biofilm sensors 120*a-b* on either side of the tibial insert 150 and a third sets of RF-based biofilm sensors 120*d* centrally located on a top of the tibial insert 150, according to some embodiments of the present disclosure.

Figure 7:
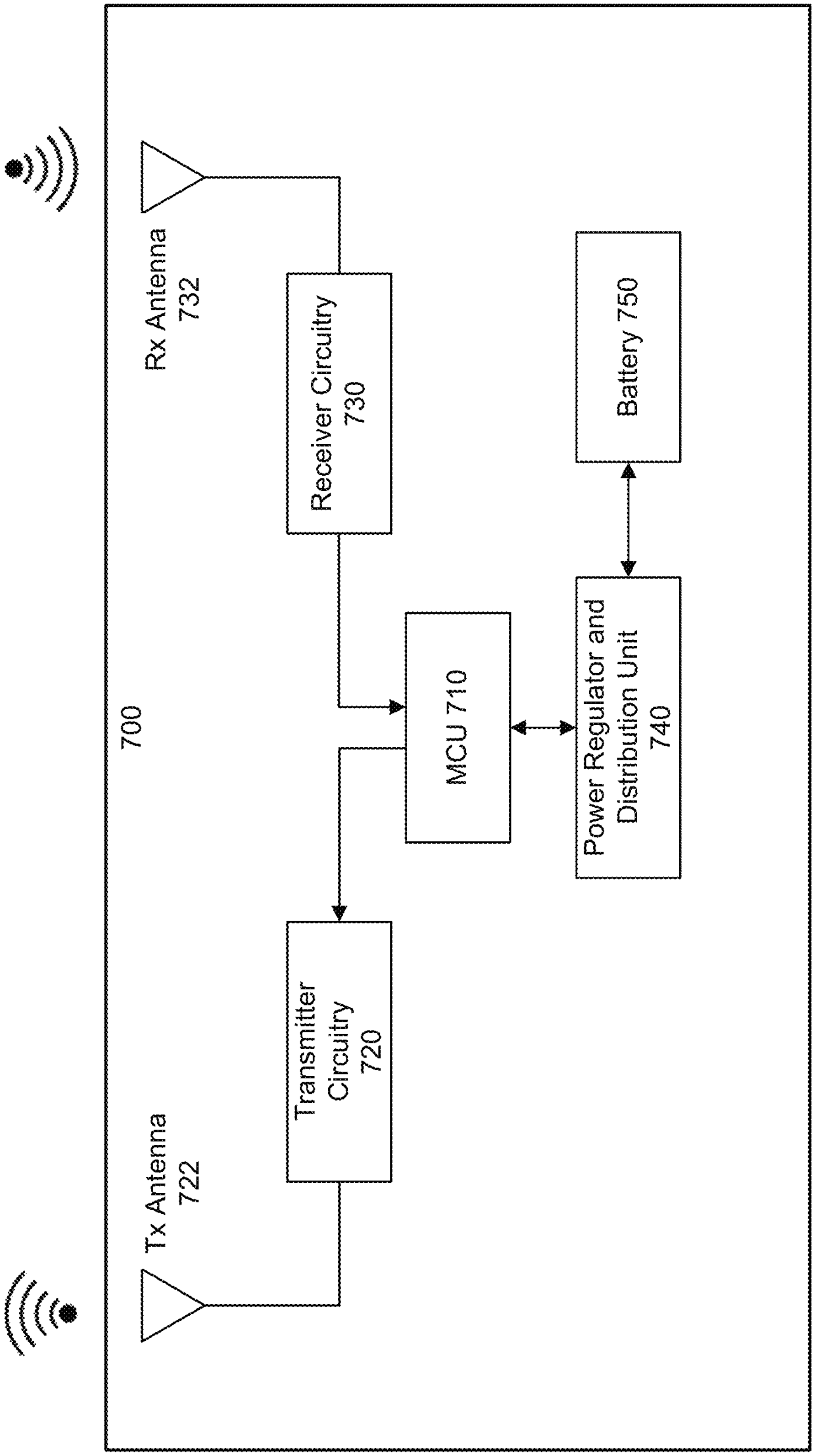
FIG. 7 illustrates a block diagram of an implantable RF-based biofilm sensor system, according to some embodiments of the present disclosure.

FIG. 7 illustrates a block diagram of an implantable RF-based biofilm sensor system 700, according to some embodiments of the present disclosure. The RF-based biofilm sensory system 700 may be housed in an implant component (e.g., tibial insert) of the medical implant and include a microcontroller unit (MCU) 710, a transmitter circuit 720, a transmit (Tx) antenna 722, a receiver circuit 730, a receiver (Rx) antenna 732, a power regulator and distribution unit 740, and a battery 750.

In some embodiments, the battery 750 may be the same or similar to energy storage device 230 of FIG. 2A. The MCU 710, power regulator and distribution unit 740, receiver circuit 730, and transmitter circuit 720 may be included in the circuitry 240 discussed above. The Tx antenna 722 may be the same or similar to the RF transmit antenna 320*a* discussed above. The Rx antenna 732 may be the same or similar to RF receive antenna 320*b* discussed above.

The battery 750 may power the other components in the RF-based biofilm sensory system 700. The power regulator and distribution unit 740 is connected to the battery 750 and the MCU 710 and may be configured, in connection with the MCU 710, to regulate and distribute power from the battery 750 to other components in the RF-based biofilm sensory system 700.

Both the Tx antenna 722 and receiver antenna 732 are connected to a processor unit (i.e., the MCU 710), which controls (i.e., generates) the transmitted RF signal and interprets the received RF signal. The MCU 710 executes a biofilm detection algorithm or instructions to process the RF signal to determine characteristics of attenuation that may indicate a presence, amount, and/or type of biofilm on the surface of the medical implant. However, a Rx antenna 732 and receiver circuit 730 may be optional, for example, in embodiments when the characteristic of attenuation of the RF signal is determined based on a reflected power of the RF signal provided by the MCU 710 toward the Tx antenna 722.

In some embodiments, the MCU may include one or more processors and may be operative to generate a RF signal to the Tx antenna 722, determine a characteristic of attenuation of the RF signal when the Tx antenna is transmitting the RF signal while implanted in the patient, and detect presence of biofilm based on the characteristic of attenuation of the RF signal.

The transmitter circuit 720 may convert power and/or signals received by the MCU 710 to signals that the Tx antenna 722 can transmit. The receiver circuit 730 may convert power and/or signals received from the Rx antenna 732 to signals the MCU 710 can receive.

In some embodiments, the Tx antenna 722 connected to a transmitter circuit 720 is capable of emitting a RF signal in the microwave RF spectrum. In a non-limiting example, the Tx antenna 722 may be able to emit a RF signal between 300 MHz and 3 GHz.

In some embodiments, the Rx antenna 732 connected to the receiver circuit 730 is operable in the same spectrum, for example, between 300 MHz and 3 GHz. The transmitted RF signal may consist of a sweep across discrete frequencies in the spectrum or a single signal at a specific frequency. In these embodiments, the MCU 710 may be further operative to generate a range of RF signals sweeping through a defined frequency range and/or a defined amplitude range, and detect the presence of biofilm based on identifying at least a threshold change in amplitude and/or frequency of the RF signals at one or more defined marker frequencies and/or defined marker amplitudes indicative of presence of a biofilm. The threshold change in amplitude and/or frequency may indicate a fingerprint for an amount and/or type of biofilm present due to certain amounts of biofilm and/or certain types (e.g., classes or species) of biofilm that attenuate the RF signal(s) at specific frequencies differently. Specific amounts (e.g., thickness and/or surface area covered, etc.) and/or types of biofilm may be known to attenuate the RF signal(s) in certain ways such as affecting the amplitude and/or frequency of the RF signal(s) (e.g., affecting impedance of the RF signal pathway) at certain frequencies. Different types of bacteria present in biofilm and/or different states of bacteria growth and biofilm formation (e.g., thickness and/or surface area covered, etc.) may be determined based on known relationships between RF transmit frequency and change in attenuation of the RF signal.

In one embodiment of the biofilm detection algorithm, the MCU 710 relates the change in frequency and change in amplitude of resonance received by the Rx antenna 732 to known states of bacteria growth and biofilm formation. The changes in these parameters are correlative to the changes in dielectric permittivity and dielectric loss of the adjacent fluid or substance associated with biofilm formation.

In some embodiments, S-parameters can be analyzed to evaluate this signal change associated with biofilm formation. According to antenna theory, S-parameters describe the input-output relationship between ports/terminals. In the RF-based biofilm sensory system 700, the transmitter circuit 720 and receiver circuit 730 would be considered ports that deliver power to the Tx antenna 722 and Rx antenna 732. Generally, the parameter Syx represents the power transferred from Port X to Port Y. In the RF-based biofilm sensory system 700, the S21 parameter represents the power transferred from Port 1 (transmitter) to Port 2 (receiver). In some embodiments, the characteristic of attenuation is the S21 parameter across a sweep of frequencies or at a specific frequency and compare the measurement to a calibration curve(s) (created as a result of performing the calibration operation(s)) associated with states of biofilm growth. Alternatively, the biofilm detection algorithm may measure the S21 parameter and compare the measurement to measurements taken over time and determine if there is a threshold difference between the S21 parameter and one or more of the measurements taken over time.

In some embodiments, the S11 parameter represents the reflected power that the transmitter circuit 720 is attempting to deliver to the Tx antenna 722. The S11 parameter is also referred to as the reflection coefficient, gamma, or return loss. Generally, antennas are designed to minimize the S11 parameter at the target frequency of use. The level of reflected power is related to impedance mismatch caused by biofilm being present, that results in bounce back of a portion of RF signal(s) conducted from the transmitter circuit 720 toward the Tx antenna 722 for transmission. S11 parameters are typically measured in dB as a function of frequency using a vector network analyzer system. In one embodiment, the RF-based biofilm sensory system 700 incorporates a vector network analyzer subsystem as part of the MCU 710 to measure the S11 parameter across a spectrum of frequencies or a specific frequency. In this configuration, the biofilm detection algorithm may measure the S11 parameter and compare the measurement to calibration curve(s) (created as a result of performing the calibration operation(s)) associated with states of biofilm growth. In these embodiments, the Rx antenna 732 and receiver circuit 730 may be optional. Alternatively, the biofilm detection algorithm may measure the S11 parameter and compare the measurement to measurements taken over time and determine if there is a threshold difference between the S11 parameter and one or more of the measurements taken over time.

In some embodiments, the MCU 710 is further operative to determine an amount of biofilm present based on the determined characteristic of attenuation of the RF signal. In some of these embodiments, the amount of biofilm present is determined proportional to an amount of attenuation of the RF signal between the RF transmit antenna (e.g., Tx antenna 722) and a RF receive antenna (e.g., Rx antenna 732) in the implant component and configured to receive the RF signal.

In some embodiments, the MCU 710 is further operative to determine a type of bacteria present in the biofilm based on the determined characteristic of attenuation of the RF signal. In some of these embodiments, the type of bacteria present in the biofilm is determined based on the characteristic of attenuation of the RF signal comprising a change in frequency of the RF signal between the RF transmit antenna and a RF receive antenna in the implant component and configured to receive the RF signal. For example, one type of bacteria or the fluid secrete therefrom can resonate at a defined frequency, and which then results in much greater attenuation of an RF signal having the defined frequency passing through the biofilm. The MCU 710 may be able to determine a type of bacteria based on observing change in the characteristic of attenuation (e.g., magnitude, phase shift, and/or frequency shift) of the RF signal when a defined RF signal frequency or range of RF signal frequencies is transmitted through that type of bacteria, where the change correlates to a known relationship attributable to that type of bacteria. Some examples of types of bacteria that may be measured or detected by the RF-based biofilm sensory system 700 include, but are not limited to, *Staphylococcus aureus, Staphylococcus epidermidis*, and *Streptococcus.*

In some embodiments, the MCU 710 is further operative to generate signaling indicating the characteristic of attenuation of the RF signal and/or indicating detection of presence of the biofilm to the RF transmit antenna (e.g., Tx antenna 722), for transmission to a clinician. For example, the MCU 710 can create a log of measured characteristics of attenuation (e.g., when a change in the measured characteristic of attenuation satisfies a defined rule) and transmit the log to a computing platform associated with the clinician, e.g., through a RF wireless link (Bluetooth) and one or more networks, e.g., public (Internet) and/or private networks. This provides the clinician with information important for diagnosis and treatment of PJI.

Further Definitions and Embodiments

It should be noted that the use of the term "characteristic" and "parameter" may be used interchangeably.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A medical implant comprising:
an implant component configured to be implanted in a patient;
a radio frequency (RF) transmit antenna in the implant component and configured to transmit a RF signal; and
circuitry within the implant component and operative to generate the RF signal to the RF transmit antenna,
determine a characteristic of attenuation of the RF signal when the RF transmit antenna is transmitting the RF signal while implanted in the patient, and
detect presence of biofilm on the medical implant based on the characteristic of attenuation of the RF signal.

2. The medical implant of claim 1, further comprising:
a RF receive antenna in the implant component and configured to receive the RF signal, and wherein the characteristic of attenuation of the RF signal is determined based on the RF signal characteristics received at the RF receive antenna.

3. The medical implant of claim 2, further comprising:
electromagnetic field (EMF) shielding positioned between the RF transmit antenna and the RF receive antenna and configured to attenuate RF signaling along a direct pathway from the RF transmit antenna to the RF receive antenna through the EMF shielding.

4. The medical implant of claim 2, wherein the RF transmit antenna and the RF receive antenna are physically spaced apart from each other along a surface of the medical implant.

5. The medical implant of claim 2, wherein the RF transmit antenna and RF receive antenna are circular shaped and arranged concentrically with different diameters.

6. The medical implant of claim 1, wherein the characteristic of attenuation of the RF signal is determined based on a reflected power of the RF signal provided by the circuitry toward the RF transmit antenna.

7. The medical implant of claim 1, wherein the characteristic of attenuation of the RF signal is determined based at least one of power transferred by the RF signal from the RF transmit antenna to a RF receive antenna in the implant component and configured to receive the RF signal, a change in frequency between the RF signal transmitted by the RF transmit antenna and the RF signal received by the RF receive antenna, and a change in amplitude between the RF signal transmitted by the RF transmit antenna and the RF signal received by the RF receive antenna, a change in phase between the RF signal transmitted by the RF transmit antenna and the RF signal received by the RF receive antenna.

8. The medical implant of claim 1, wherein the detection of the presence of biofilm comprises to compare the determined characteristic of attenuation of the RF signal to a threshold characteristic of attenuation defined based on a calibration measurement operation.

9. The medical implant of claim 1, wherein the detection of the presence of biofilm comprises to compare the characteristic of attenuation of the RF signal to at least one prior characteristic of attenuation, and determine that biofilm is present based on the characteristic of attenuation of the RF signal being a threshold difference than the prior characteristic of attenuation.

10. The medical implant of claim 1, wherein the circuitry is further operative to:
generate a range of RF signals sweeping through a defined frequency range and/or a defined amplitude range; and
detect the presence of biofilm based on identifying at least a threshold change in amplitude and/or frequency of the RF signals at one or more defined marker frequencies and/or defined marker amplitudes indicative of presence of a biofilm.

11. The medical implant of claim 1, wherein the circuitry is further operative to determine an amount of biofilm present based on the determined characteristic of attenuation of the RF signal.

12. The medical implant of claim 11, wherein the amount of biofilm present is determined proportional to an amount of attenuation of the RF signal between the RF transmit antenna and a RF receive antenna in the implant component and configured to receive the RF signal.

13. The medical implant of claim 1, wherein the circuitry is further operative to determine a type of bacteria present in the biofilm based on the determined characteristic of attenuation of the RF signal.

14. The medical implant of claim 13, wherein the type of bacteria present in the biofilm is determined based on the characteristic of attenuation of the RF signal comprising a change in frequency of the RF signal between the RF transmit antenna and a RF receive antenna in the implant component and configured to receive the RF signal.

15. The medical implant of claim 1,
wherein the RF transmit antenna is recessed in the implant component, and further comprising a RF window extending across the RF transmit antenna and separating the antenna from fluid and/or tissue while the medical implant is implanted in the patient.

16. The medical implant of claim 15, wherein the RF window has a rougher surface, exposed to the patient, than an adjacent surface of the implant component exposed to the patient to promote earlier formation of biofilm on the rougher surface of the RF window.

17. The medical implant of claim 1, wherein circuitry is further operative to generate signaling indicating the characteristic of attenuation of the RF signal and/or indicating detection of presence of the biofilm to the RF transmit antenna, for transmission to a clinician.

* * * * *